(12) United States Patent
Gershow et al.

(10) Patent No.: US 8,273,532 B2
(45) Date of Patent: Sep. 25, 2012

(54) CAPTURE, RECAPTURE, AND TRAPPING OF MOLECULES WITH A NANOPORE

(75) Inventors: Marc H. Gershow, Somerville, MA (US); Jene A. Golovchenko, Lexington, MA (US); Daniel Branton, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 310 days.

(21) Appl. No.: 12/286,787

(22) Filed: Oct. 2, 2008

(65) Prior Publication Data

US 2009/0136958 A1    May 28, 2009

Related U.S. Application Data

(60) Provisional application No. 60/997,322, filed on Oct. 2, 2007.

(51) Int. Cl.
  *C12Q 1/68* (2006.01)
  *C12M 1/00* (2006.01)
  *G01N 15/06* (2006.01)
  *C07H 21/04* (2006.01)

(52) U.S. Cl. .................. 435/6.1; 435/283.1; 435/258.2; 435/286.1; 435/288.5; 422/68.1; 422/82.01; 536/23.1; 977/924; 977/932; 977/953; 977/958

(58) Field of Classification Search .................. None
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |
| 6,413,792 B1 | 7/2002 | Sauer et al. | |
| 6,627,067 B1 | 9/2003 | Branton et al. | |
| 6,870,361 B2 | 3/2005 | Chopra et al. | |
| 6,919,002 B2 | 7/2005 | Chopra | |
| 7,001,792 B2 | 2/2006 | Sauer et al. | |
| 7,005,264 B2 | 2/2006 | Su et al. | |
| 7,189,503 B2 | 3/2007 | Akeson et al. | |

(Continued)

FOREIGN PATENT DOCUMENTS

AU    2006336262    7/2007

(Continued)

OTHER PUBLICATIONS

PCT International Search Report and Written Opinion of the International Searching Authority for International Application No. PCT/US2008/011412, whole document, Jan. 29, 2009.

(Continued)

*Primary Examiner* — Betty Forman
(74) *Attorney, Agent, or Firm* — Theresa A. Lober

(57) ABSTRACT

In a molecular analysis system, there is provided a structure including a nanopore and first and second fluidic reservoirs. The two reservoirs are fluidically connected via the nanopore. A detector is connected to detect molecular species translocation of the nanopore, from one of the two fluidic reservoirs to the other of the two fluidic reservoirs. A controller is connected to generate a control signal to produce conditions at the nanopore to induce the molecular species to re-translocate the nanopore at least once after translocating the nanopore. This enables a method for molecular analysis in which a molecular species is translocated a plurality of times through a nanopore in a structure between two fluidic reservoirs separated by the structure.

71 Claims, 10 Drawing Sheets

U.S. PATENT DOCUMENTS

| | | | |
|---|---|---|---|
| 7,468,271 B2 * | 12/2008 | Golovchenko et al. | 435/287.2 |
| 7,803,607 B2 * | 9/2010 | Branton et al. | 435/287.2 |
| 2002/0127144 A1 * | 9/2002 | Mehta | 422/81 |
| 2003/0141189 A1 | 7/2003 | Lee et al. | |
| 2006/0068401 A1 | 3/2006 | Flory et al. | |
| 2006/0073489 A1 * | 4/2006 | Li et al. | 435/6 |

FOREIGN PATENT DOCUMENTS

| | | |
|---|---|---|
| EP | 1443318 | 8/2004 |
| WO | WO2004035211 | 4/2004 |
| WO | WO2007041621 | 4/2007 |
| WO | WO2008124107 | 10/2008 |

OTHER PUBLICATIONS

European Patent Office Communication for EP Application No. 08834957.6-1222, PCT/US2008/011412, whole document, May 18, 2010.

Response to European Patent Office Communication for EP Application No. 08834957.6-1222, PCT/US2008/011412, whole document, Jun. 28, 2010.

European Patent Office Communication for EP Application No. 08834957.6-1222. PCT/US2008/011412, whole document, Oct. 19, 2010.

Intellectual Property Office of New Zealand Communication for Patent Application No. 584571, PCT/US2008/011412, whole document, Dec. 8, 2010.

Fologea et al., "Detecting Single Stranded DNA with a Solid State Nanopore," Nano Letters, vol. 5, No. 10, pp. 1905-1090, Aug. 31, 2005.

Meller et al., "Rapid nanopore discrimination between single polynucleotide molecules," PHAS, vol. 97, No. 3, pp. 1079-1084, Feb. 1, 2000.

Li et al., "DNA molecules and configurations in a solid-state nanopore microscope," Nature Materials, vol. 2, pp. 611-615, Sep. 2003.

King et al., "Probing Nanotube-Nanopore Interactions," Phys. Rev. Letts., V. 95, pp. 216103-1-216103-3, Nov. 18, 2005.

Deamer et al., "Characterization of Nucleic Acids by Nanopore Analysis," Acc. Chem. Res. vol. 36, pp. 817-825, Sep. 27, 2002.

Wang et al., "Nanopores with a spark for single-molecule detection," Nature Biotechnology, vol. 19, pp. 622-623, Jul. 2001.

Sauer-Budge et al., "Unzipping Kinetics of Double-Stranded DNA in a Nanopore," Phys. Rev. Letts., vol. 90, No. 23, pp. 238101-1-238101-4, Jun. 13, 2003.

Kasianowicz et al., "Characterization of individual polynucleotide molecules using a membrane channel," Proc. Natl. Acad. Sci. USA, vol. 93, pp. 13770-13773, Nov. 1996.

Chen et al., "Probing Single DNA Molecule Transport Using Fabricated Nanopores," Nano Letters, vol. 4, No. 11, pp. 2293-2298, Oct. 26, 2004.

Meller et al., "Single molecule measurements of DNA transport through a nanopore," Electrophoresis, vol. 23, pp. 2583-2591, 2002.

Meller et al., "Voltage-Driven DNA Translocation through a Nanopore," Phys. Rev. Letts., vol. 86, No. 15, pp. 3435-3438, Apr. 9, 2001.

Branton et al., "Adapting to nanoscale events," Nature, vol. 398, pp. 660-661, Apr. 22, 1999.

Hornblower et al., "Single-molecule analysis of DNA-protein complexes using nanopores," Nature Methods, vol. 4, No. 4, pp. 315-317, Apr. 2007.

Saleh et al, "An artificial Nanopore for Molecular Sensing," Nano Letters, vol. 3, No. 3, pp. 37-38, Dec. 3, 2002.

Chang et al., "DNA-mediated Fluctuations in Ionic Current through Silicon Oxide Nanopore Channels," Nano Letters, vol. 4, No. 8, pp. 1551-1556, Jul. 7, 2004.

Nakane et al., "A Nanosensor for Transmembrane Capture and Identification of Single Nucleic Acid Molecules," Biophysical Jnl., vol. 87, pp. 615-621, Jul. 2004.

Meller, Dynamics of polynucleotide transport through nanometre-scale pores, J. Phys.:Condens. Matter, vol. 15, pp. R581-R607, IOP Publ. Ltd, UK, Apr. 22, 2003.

Gershow et al., "Recapturing and trapping single molecules with a solid-state nanopore," Nature Nanotechnology, vol. 2, pp. 775-779, Dec. 2, 2007.

Bates et al., "Dynamics of DNA Molecules in a Membrane Channel Probed by Active Control Techniques," Biophysical Jnl., vol. 84, pp. 2366-2372, Apr. 2003.

Nakane et al., "Nanopore sensors for nucleic acid analysis," J. Phys.: Condens. Matter vol. 15, pp. R1365-R1393, IOP Publ. Ltd., UK, Aug. 1, 2003.

* cited by examiner

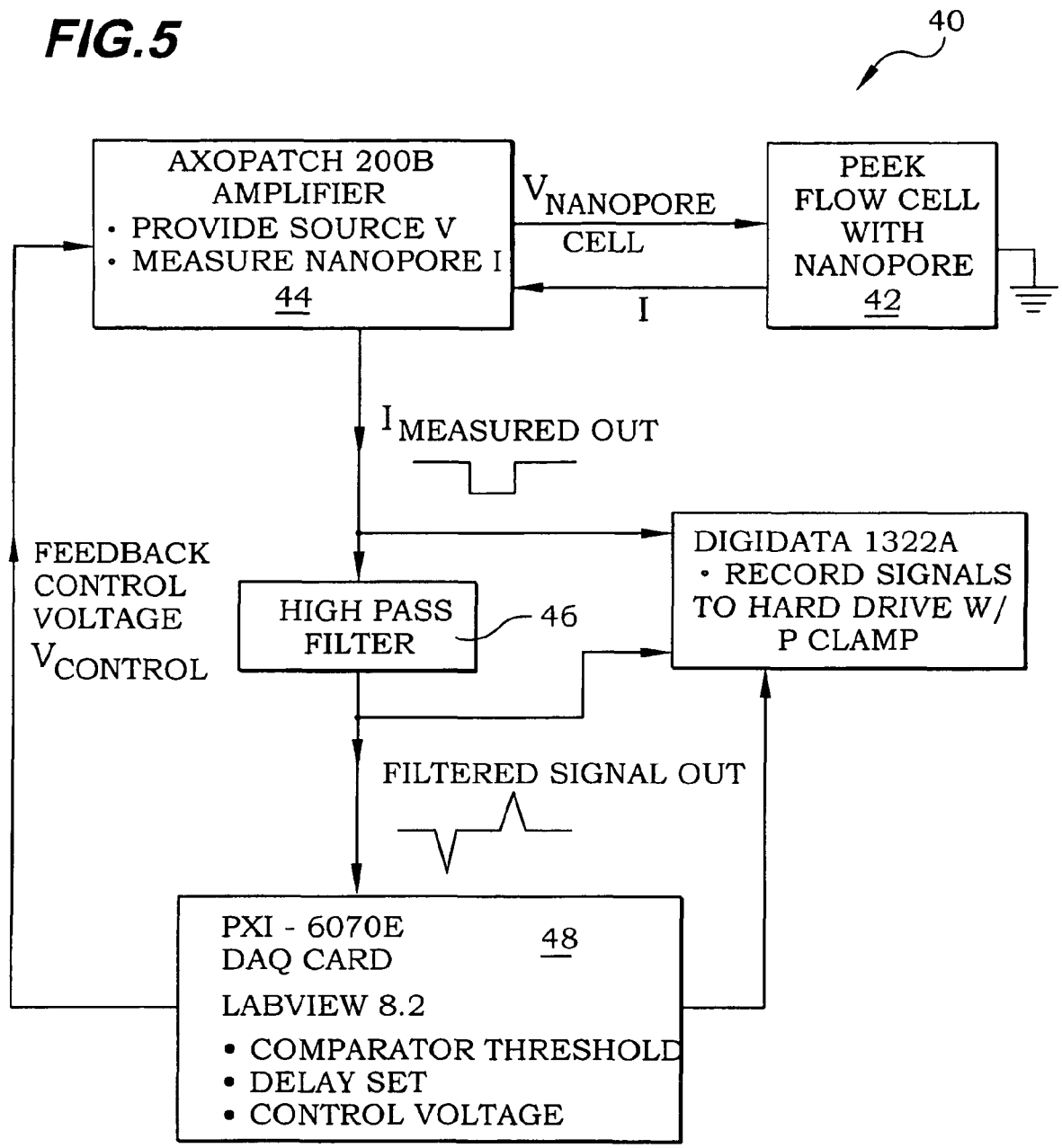

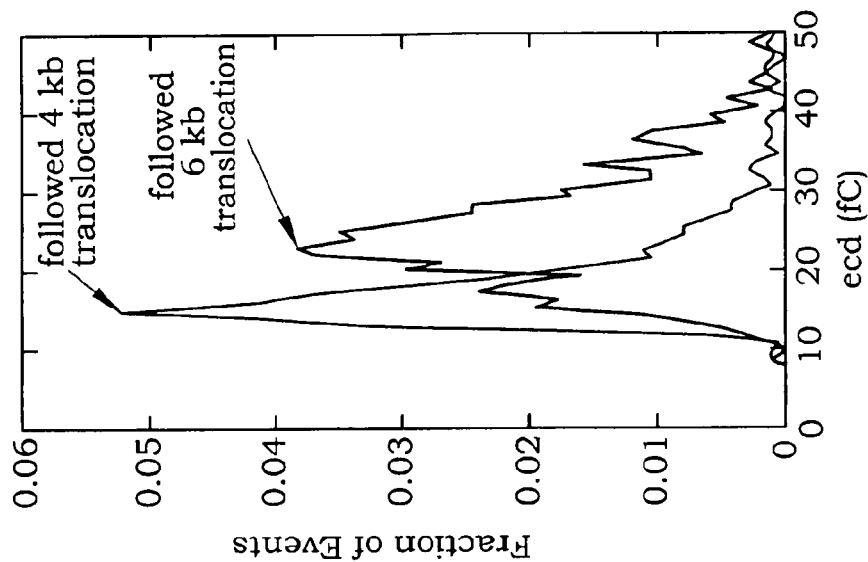
FIG.7A ECD Histogram - Forward Translocations
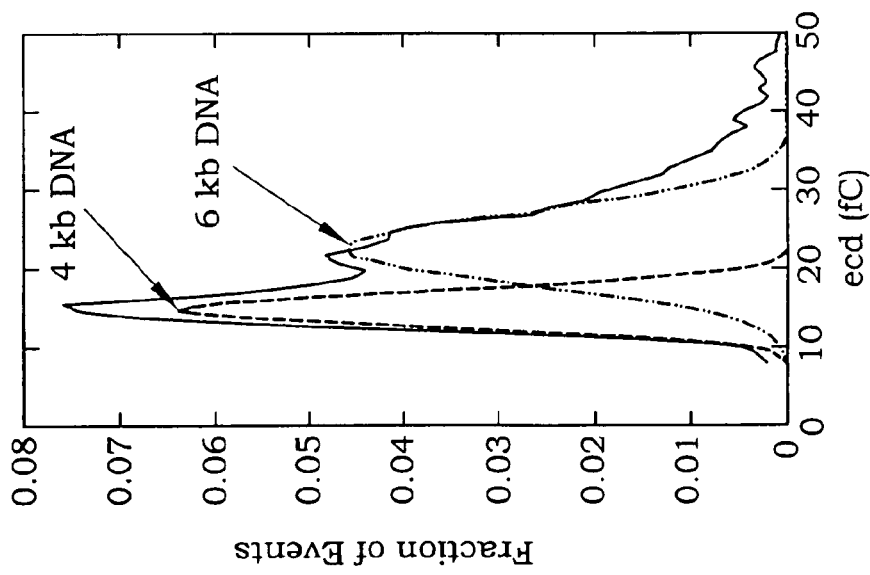
FIG.7B ECD Histogram - Selected Reverse Translocations Recapture Success Rate vs. $t_{delay}$ Capture Rate vs. Time Since Voltage Flip

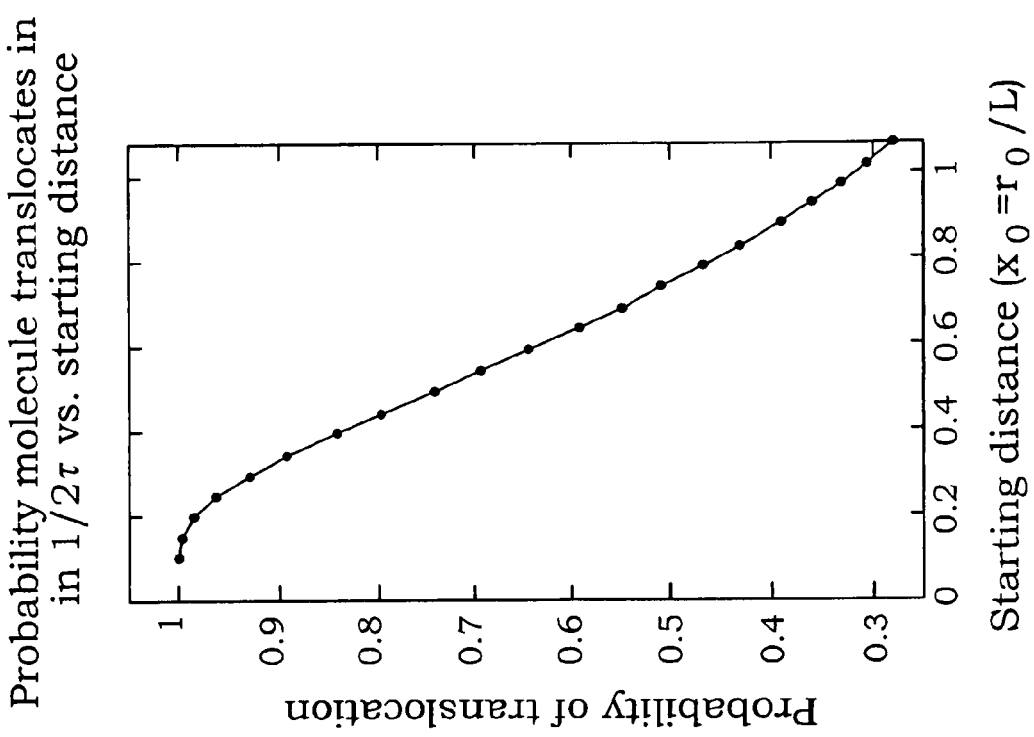
FIG.11B Probability molecule translocates in $1/2\tau$ vs. starting distance
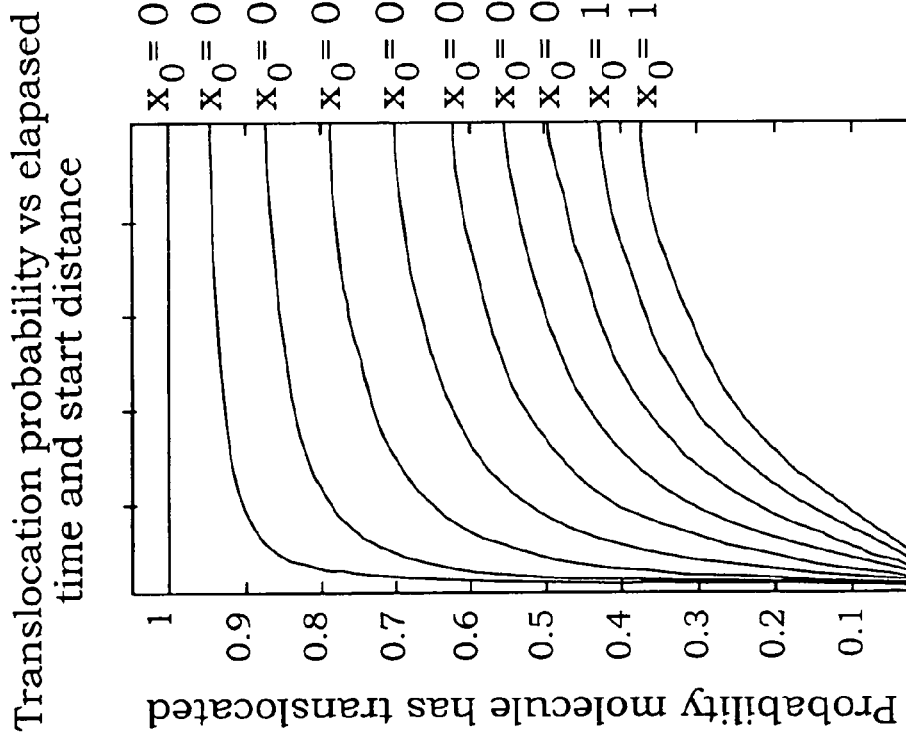
FIG.11A Translocation probability vs elapased time and start distance

CAPTURE, RECAPTURE, AND TRAPPING OF MOLECULES WITH A NANOPORE

RELATED APPLICATIONS

This application claims the benefit of U.S. Provisional Application No. 60/997,322, filed Oct. 2, 2007, the entirety of which is hereby incorporated by reference.

STATEMENT REGARDING FEDERALLY SPONSORED RESEARCH

This invention was made with Government support under Contract No. 5RO0HG003703, awarded by NIH. The Government has certain rights in the invention.

BACKGROUND OF INVENTION

This invention relates generally to the detection and characterization of molecules, and more particularly relates to nanopore device configurations and corresponding techniques for the characterization of molecules.

The detection, analysis, and quantification of molecules, and particularly biological molecules, has become important for a wide range of applications, e.g., in the areas of healthcare and the life sciences. Of particular interest is an ability to carry out single molecule sensing. The development of solid state nanopores has shown great potential for the characterization of single macromolecules and especially biological molecules like proteins and DNA. Applications of such characterization include, e.g., the analysis of protein folding and the sequencing of DNA, among other applications.

Considering, e.g., the sequencing of DNA by a solid state nanopore, DNA molecules, e.g., single stranded DNA (ssDNA), are threaded through a nanopore and analyzed base by base along the strand as an electric field or other driving force causes translocation of the DNA from, e.g., a source reservoir of ionic solution through the nanopore to a collection reservoir of ionic solution. Despite intense research interest, such DNA capture by a solid state nanopore and translocation through the nanopore is currently not well understood. Indeed, in general the specific interaction with and motion at a nanopore has yet to be ascertained at the molecular level. In-depth characterization of single molecules with a nanopore, either alone or as part of a more complicated device, cannot be accomplished until a more full understanding and the control of the dynamics of a molecule's interaction with a nanopore are achieved.

SUMMARY OF THE INVENTION

The invention provides nanopore device configurations and techniques for employing such configurations to enable single molecule manipulation and characterization with a nanopore. In one example configuration in accordance with the invention for molecular analysis system, there is provided a structure including a nanopore and first and second fluidic reservoirs. The two reservoirs are fluidically connected via the nanopore. A detector is connected to detect molecular species translocation of the nanopore, from one of the two fluidic reservoirs to the other of the two fluidic reservoirs. A controller is connected to generate a control signal to produce conditions at the nanopore to induce the molecular species to re-translocate the nanopore at least once after translocating the nanopore.

With this system, a molecular species, such as a molecule or component of a molecule, can be captured, recaptured, and analyzed with regard to the conditions of the nanopore and conditions of the first and second reservoirs. As explained in detail below, the invention thereby enables a wide range of experiments and analyses that elucidate the nature of molecular behavior. The molecular capture and recapture control system provides knowledge of a molecule's position at a nanopore at both ends of a measured time interval, and provides knowledge of the forces applied to the molecule during that time interval, enabling an evaluation of the molecule's path in solution. The dynamics of a molecule reaching a nanopore can therefore be correlated with the dynamics of a molecule entering a nanopore, and each activity can be studied individually.

Thus, the invention provides a method for molecular analysis in which a molecular species is translocated a plurality of times through a nanopore in a structure between two fluidic reservoirs separated by the structure.

This technique of the invention enables a method for exposing a molecular species to a reactive environment, by translocating a molecular species through a nanopore from a first fluidic reservoir to a second fluidic reservoir containing an environment that is reactive with the molecular species, and producing conditions at the nanopore to induce molecular re-translocation of the nanopore from the second fluidic reservoir back to the first fluidic reservoir.

This technique of the invention further enables a method for spatially trapping a molecular species, by translocating a molecular species a plurality of times through a nanopore in a structure between two fluidic reservoirs separated by the structure, and applying trapping conditions at the nanopore to maintain the molecular species in one of the two reservoirs in a vicinity of the nanopore between each molecular species translation of the nanopore.

Further is enabled by the invention a method for sequencing a genome. In this method, there is provided a plurality of nucleotide fragments from a genome in a first fluidic reservoir. Each nucleotide fragment is translocated a selected number of times through a nanopore in a structure between the first fluidic reservoir and a second fluidic reservoir separated from the first reservoir by the structure Each nucleotide fragment is detected as that nucleotide fragment translocates the nanopore.

Other features and advantages of the invention will be apparent from the following description and accompanying figures, and from the claims.

BRIEF DESCRIPTION OF THE DRAWINGS

FIG. 5 is a block diagram of a feedback control loop for operating the nanopore-based molecular capture and recapture system of the invention;

FIGS. 7A-7B are histogram plots of the measured time integral of measured ionic blockage current, known as the event charge deficit, for forward translocation of a nanopore, and for reverse translocation of a nanopore, respectively, in an experimental molecular capture and recapture system in accordance with the invention;

FIGS. 11A-11B are plots of the calculated probability of molecular translocation of a nanopore as a function of time and distance, for an experimental molecular capture and recapture system in accordance with the invention.

DETAILED DESCRIPTION OF THE INVENTION

Referring to FIGS. 1A-1F, there are schematically represented views of a molecule as the molecule interacts with a nanopore, with the views shown at selected times during a process of capture and recapture of the molecule at the nanopore in an example method provided by the invention. A molecule 10 is provided in a supply, or cis, reservoir 12 for interaction with a nanopore 14. A collection, or trans, reservoir 16 is provided on an opposite side of the nanopore 14 for accepting molecules from the nanopore.

Figure 1A:
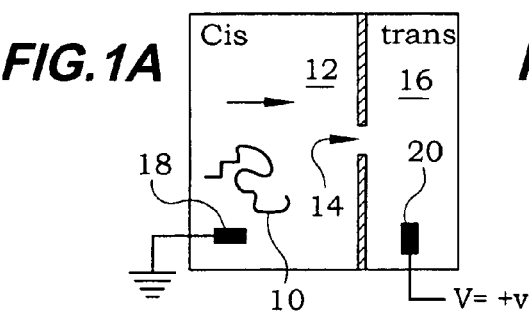
FIGS. 1A-1F are schematic views of a molecule interacting with a nanopore at various selected points in time during an example technique provided by the invention for capture and recapture of a molecule by a nanopore.

In one example arrangement, the cis and trans reservoirs are provided with an ionic solution that can pass between the reservoirs by way of the nanopore. Electrodes 18, 20 provided in the cis and trans reservoirs make electrical contact to the solution in the reservoirs and therefore enable the application of a selected voltage across or current flow between the reservoirs, creating an electric field in the vicinity of the nanopore 14 in each reservoir. One reservoir, e.g., the cis reservoir as shown in FIG. 1A, is held at electrical ground potential, with a selected voltage applied to the trans reservoir.

In a first capture step, the trans reservoir voltage is set to translocate the molecule through the nanopore 14. In the example of FIG. 1 it is assumed that the molecule is negatively charged. A positive voltage applied to the trans reservoir therefore produces an electric force on the molecule toward the trans reservoir, through the nanopore, as indicated by the arrow in the cis reservoir in FIG. 1A. The molecule moves from the bulk solution of the cis reservoir to the vicinity of the nanopore 14 by a combination of Brownian and electrophoretic motion.

Figure 1B:
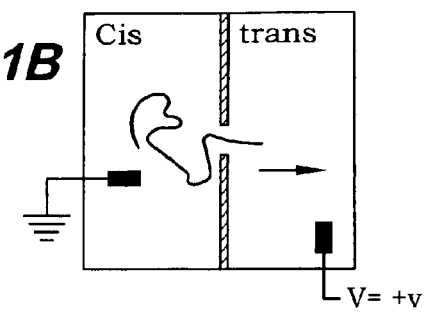
Figure 1C:
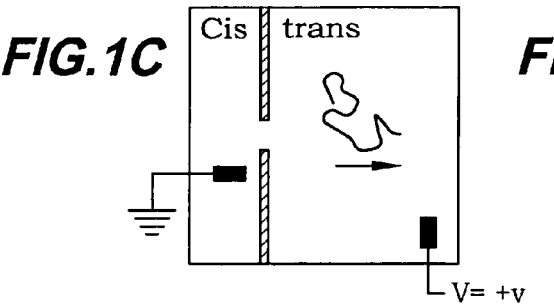

Referring to FIG. 1B, once the molecule reaches the nanopore, the molecule may enter the nanopore and pass completely through the nanopore, i.e., may translocate the nanopore to the trans reservoir, due to the electrophoretic force caused by the applied voltage. As shown in FIG. 1C, after translocating the nanopore, the molecule continues to move under the influence of the nanopore's proximal electric field, as well as thermal and diffusive forces, driving the molecule away from the nanopore, toward the bulk solution of the trans reservoir.

Figure 1D:
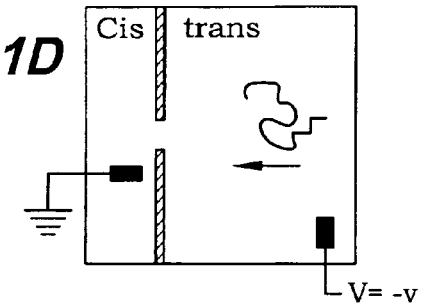
Figure 1E:
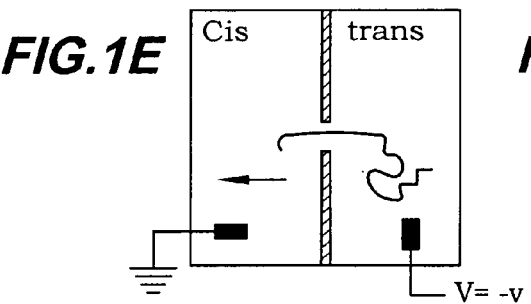

To recapture the molecule, the driving force across the nanopore is reversed before the molecule can escape into the bulk solution of the trans reservoir. As shown in FIG. 1D, given a negatively charged molecule, the trans reservoir voltage is then reversed to negative polarity, whereby the electrophoretic force on the molecule is now directed back to the nanopore. With this configuration, as shown in FIG. 1E, the molecule re-translocates the nanopore back to the cis reservoir.

Figure 1F:
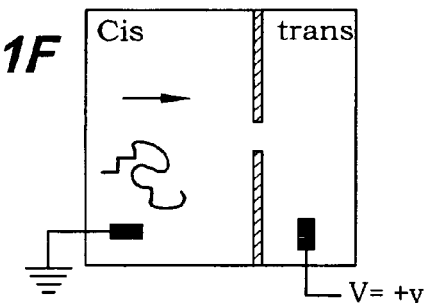

The recaptured molecule, now having translocated the nanopore in the reverse of its original direction, can then be captured a third time by, as shown in FIG. 1F, by restoring the driving voltage to its original polarity, producing an electrophoretic force again toward the nanopore. This molecular capture at the nanopore, and passage between the cis and trans reservoirs, can be repeated any number of times unless or until the molecule escapes from the vicinity of the nanopore, into the bulk of a reservoir solution.

In accordance with the invention, the capture and recapture of a molecule at the nanopore is detected and controlled based on the needs of a given application or experiment. In general, the passage of a molecule through the nanopore can be detected by any convenient technique, as described in general detail below. For purposes of general introduction, a first example detection technique is described here as detection of a blockage, by the molecule, of the ionic current flowing between the cis and trans reservoirs through the nanopore. During translocation, the molecule partially obstructs the flow of ionic solution through the nanopore, increasing the impedance of the nanopore and reducing the corresponding ionic current through the nanopore. Thereby, measurement of electrical current in a closed circuit between the electrodes of the two reservoirs provides an indication of such reduced ionic current flow.

Figure 2:
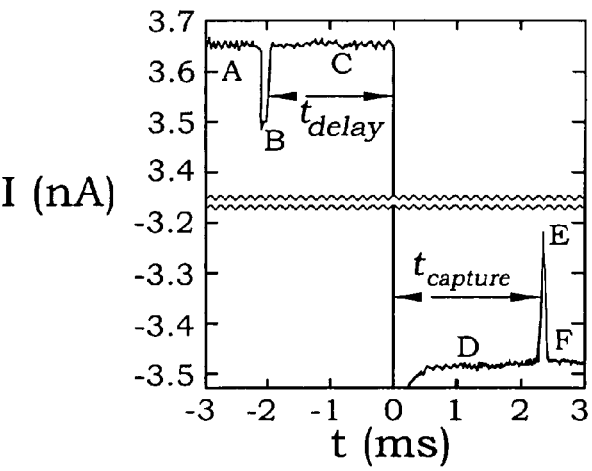
FIG. 2 is a plot of measured ionic current through a nanopore as a function of time for the molecular capture and recapture technique of FIGS. 1A-1F, identifying the current measurements corresponding to views of FIGS. 1A-1F.

FIG. 2 is an example plot of measured ionic current as a function of time for an experimental system employing the capture and recapture processes of FIGS. 1A-1F. For clarity, 6.6. nA of current have been excised from the middle of the plot. As shown in the plot, during a first interval, A, in which the molecule is in the cis reservoir, as in FIG. 1A, a current level corresponding to an open nanopore is measured. Then at time B, a reduction in current is measured, corresponding to a blockage in ionic current by a molecule translocating the nanopore as in FIG. 1B. Once the current blockage is detected, there is imposed a delay period, $t_{delay}$, interval C, before the voltage is reversed to recapture the molecule. During the delay period, as shown in FIG. 1C, the molecule is driven away from the nanopore and the measured current indicates an empty nanopore. In the example of FIG. 2, the delay period, $t_{delay}$, is set at 2 ms.

At the end of the delay period, the voltage is reversed to recapture the molecule and during this re-capture period, $t_{capture}$, interval D, the molecule is driven back to the nanopore, as in FIG. 1D, and the measured current indicates an empty nanopore. At time E a reduction in current is again measured, corresponding to a blockage in ionic current by the recaptured molecule translocating the nanopore back to the cis reservoir as in FIG. 1E. In interval F the molecule is again in the cis reservoir, awaiting additional capture events, as in FIG. 1F. The intervals A and D, in which the applied voltage is set to drive the molecule toward the nanopore, from the cis reservoir to the trans reservoir and from the trans reservoir to the cis reservoir, respectively, can be varied or can be fixed to enable a selected molecular experiment or analysis, as described in detail below. Also as described in detail below, the delay interval C before the driving voltage polarity is reversed, can also be varied to achieve a selected experimental or analytical condition.

With this control sequence, a molecule can be captured, recaptured, and analyzed with regard to the conditions of the nanopore and conditions of the cis and trans reservoirs. As explained in detail below, the invention thereby enables a wide range of experiments and analyses that elucidate the nature of molecular behavior. The molecular capture and recapture control sequence provides knowledge of a molecule's position at a nanopore at both ends of a measured time interval, and provides knowledge of the forces applied to the molecule during that time interval, enabling an evaluation of the molecule's path in solution. The dynamics of a molecule reaching a nanopore can therefore be correlated with the dynamics of a molecule entering a nanopore, and each activity can be studied individually.

The term "molecule" is herein meant to refer to a complete molecular entity, such as a DNA strand. The term "molecular component" is herein meant to refer to a subunit, or component, of a molecule. For example, a nucleotide is a molecular subunit of a DNA molecule. Each of the four DNA bases form four distinct nucleotide types. Molecular components can be, in one example, sequential, individual, distinct entities that together form a molecule. The molecular capture and recapture control sequence can be applied to molecules, molecular components, or other molecular species to be characterized by translocation of a nanopore.

Figure 3:
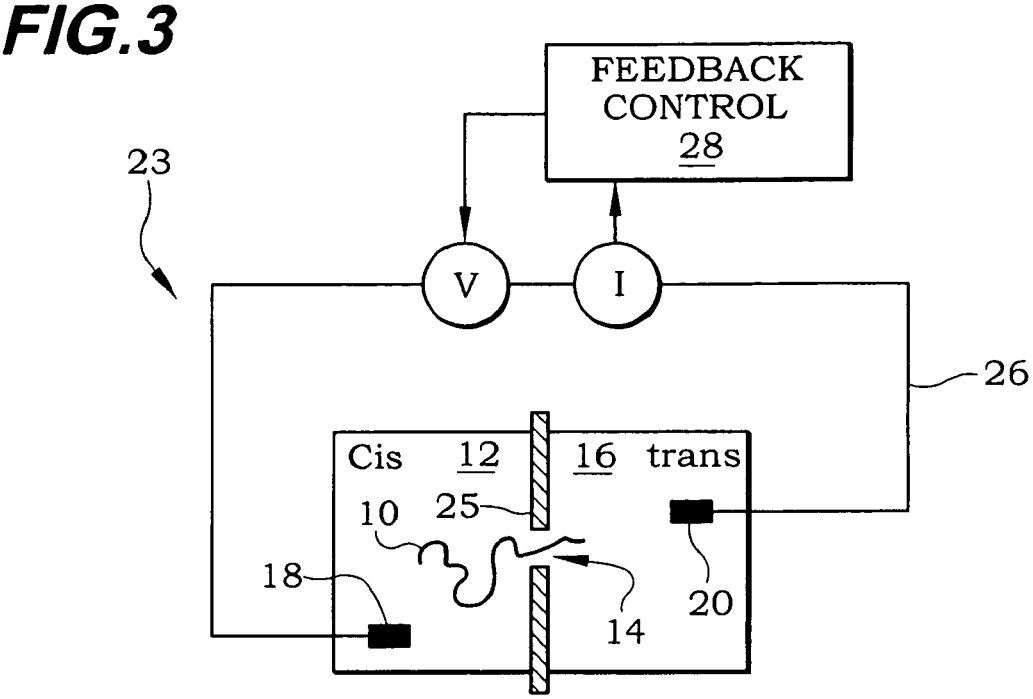
FIG. 3 is a schematic view of an example nanopore system configuration provided by the invention for enabling the molecular capture and recapture technique of FIGS. 1A-1F.

Turning to aspects of the molecular capture system of the invention, an example implementation of the molecular capture system 23 is provided schematically in FIG. 3. The system includes a structure 25 in which is provided an aperture, pore, hole, channel, via, or other opening for translocation of molecules. For many applications, a nanopore 14 can be preferred. The term "nanopore" here refers to an aperture or opening having a diameter that is generally less than about 1 micron.

In accordance with the invention, the diameter, or extent, of the nanopore is selected to achieve a desired molecular condition. In one example nanopore selection, the nanopore diameter is sufficiently small to require that a molecule be linearized, i.e., the portion of the molecule that is within the confining volume of the nanopore includes no secondary or higher structure, during its passage through the nanopore. Once through the nanopore, the linearized molecule will typically begin to condense, either in an ordered or disordered fashion. As a result, through measurement of changes in duration in molecular translocation of the nanopore as a function of, e.g., the duration of delay before molecular recapture, or the direction of passage, there can be determined the time period in which molecular condensing events, e.g., nucleic acid or protein folding, begin or are completed.

As shown by this example, the nanopore extent can be tailored for a selected analysis or molecular structure. In general, the nanopore diameter is no greater than about 1 micron, preferably no greater than about 100 nm, more preferably no greater than 10 nm or 5 nm. If, e.g., dsDNA is to linearly translocate a nanopore, then a nanopore diameter of, e.g., between about 3 nm and about 10 nm can be preferred. If ssDNA is to linearly translocate a nanopore, then a nanopore diameter less than about 5 nm can be preferred. The nanopore diameter is also selected in concert with the molecular driving force, to enable a selected molecular configuration during translocation. For example, for a given electric field to produce an electrophoretic force on a molecule, the nanopore diameter can be selected to enable recapture of molecules while requiring the molecules to translocate the nanopore without bending. Thus, the nanopore diameter is tailored to the conditions of a molecule of interest, and any molecule whose movement through a suitably-sized nanopore can be characterized repeatedly by the capture and recapture techniques of the invention.

The nanopore diameter can be selected to allow or to disallow secondary or higher structure in a molecule as the molecule traverses the nanopore, as-prescribed for a given application. When the nanopore only allows primary structure, the transport properties measured, e.g., the time required to traverse the nanopore, may be indicative of the strength of any secondary or higher structure present prior to traversing the nanopore. When the nanopore allows secondary or higher structure to translocate, the transport properties measured may be indicative of the presence, absence, or location of such secondary or higher structure. For example, for a nanopore that allows the passage of dsDNA to translocate, the location of a complementary oligomer bound to ssDNA strand may be determined during a recapture event based on the time that a change in transport properties between the capture and recapture events occurs relative to the beginning and end of the single stranded nucleic acid traversing the pore.

The nanopore capture and recapture processes can be employed with naturally occurring or synthetic molecules. Biomolecules, e.g., polymers including nucleic acids such as single-stranded or double-stranded DNA and RNA, proteins, polysaccharides, lipids, and synthetic polymers all are particularly well-addressed by the nanopore capture and recapture processes of the invention. The nanopore capture and recapture processes can further be applied to a species that consists of one or more portions of a full molecule, e.g., by application to a component of a molecule such as an oligonucleotide or sequence of DNA bases. Thus the invention is not limited to a specific molecule, species, or component of a molecule, and is not limited to a particular nanopore extent or geometry. Generally circular, angular, or other nanopore geometry can be employed, provided through the thickness of a structure 25, as-suitable for a selected molecule or species to be analyzed.

The structure 25 can be implemented as a substrate, chip, suspended layer, membrane, or other structure in which a generally microscale-to-nanoscale length of a nanopore can be achieved between two surfaces of the structure separating the cis and trans reservoirs. Herein the term "membrane" refers to a generally thin layer of material that is self-supported across its extent and is supported at its edges by, e.g., a structural frame such as a substrate. The structure can be electrically insulating, conducting, or semiconducting, as-required for a given application and selected translocation detection mechanism, for example, as a microelectronic material, as described below. The cis and trans reservoirs 12, 16 can be provided in concert with the structure as flow channels, fluidic inlets and outlets or ports, or other fluidic structures, for enabling delivery of a fluid in the reservoir to a nanopore for interaction of species in the fluid with the nanopore.

As explained above, in one example implementation, an applied driving force field is provided in each of the reservoirs, in the vicinity of the nanopore, to induce molecular species in one reservoir to translocate the nanopore. In the example of FIG. 1, electrodes are 18, 20 are provided in the reservoirs to apply a voltage across or a current flow through the nanopore by virtue of electrical charges in the reservoir solution, e.g., an ionic solution including electrically charged molecules. This electrophoretic force can be well-controlled by voltage application, as described in detail below.

The invention provides a wide range of alternative driving force field mechanisms. If the nanopore is provided as an aperture of sufficient diameter, fluid flow from an external reservoir can provide the driving force. For small but electrically neutral molecular species to be analyzed, electroosmotic flow generated in the nanopore by an applied voltage or current can provide the requisite driving force. Additionally, hydrodynamic pressure, magnetic force for, e.g., molecules labeled with a magnetic moiety, optical trapping, and mechanical force, e.g., with a probe such as an atomic force microscope tip, can be employed. Whatever translocation force is employed, such preferably enables reversal in directionality between the reservoirs to enable multiple molecular recapture and trapping events.

As shown in FIG. 3, in one example implementation employing electrophoretic force in the manner described above, a voltage, V, is applied between the reservoirs as part of an electrical feedback control circuit 26. The voltage to be applied is preferably of a magnitude that is sufficient to draw molecular species from a bulk reservoir solution to the vicinity of the nanopore.

The force on a molecule that is produced by this voltage application can be modeled for determining characteristic voltage levels and molecular behavior in response to those voltage levels. For example, given the macromolecule DNA, the motion of a strand of DNA can be modeled based on the electric force from an applied voltage on the charged phosphate backbone and random thermal forces due to collisions with fluidic molecules in the reservoirs. Competition between thermal and electrical forces sets a characteristic distance between a nanopore and the molecule below which the electrical force is more likely to dominate over thermal and diffusive forces.

In an example model, it is assumed that on average, diffusion drives a molecule radially away from a nanopore, which for modeling is identified as being located at a site r=0. Then a radial diffusion velocity, $v_d(r)$, can be defined as $v_d(r)=D/r$, where D is the diffusion constant of the DNA strand. An electrical ionic current density, J, results from an electric field, E, given by $J=\sigma E$, where $\sigma$ is the electrical ionic conductivity of the reservoir solution, e.g., an ionic solution. In a reservoir at distances away from the nanopore that are much greater than the diameter of the nanopore, the current density and electric field will be hemispherically symmetric, and related to the measured ionic current, I, through the voltage-biased nanopore as $$E(r) = \frac{J(r)}{\sigma} = \frac{I\hat{r}}{2\pi r^2 \sigma}.$$

DNA strands in free solution are known to move with a velocity based on a characteristic electrophoretic mobility, $\mu$. If the conformational degrees of freedom of a DNA strand are ignored and it is assumed that the electrical charge of the DNA strand is distributed symmetrically about its center of mass, located at r, then the radial electrophoretic velocity, $v_e(r, t)$ is given as $$v_e = \frac{\mu I}{2\pi r^2 \sigma}.$$

Now, comparing this electrophoretic velocity, $v_e(r, t)$, with the diffusion velocity, $v_d(r)$, it is found that there exists a characteristic distance, L, where $$L = \frac{|\mu I|}{2\pi\sigma D},$$

beyond which the average velocity of the DNA strand away from the nanopore, due to diffusion, is greater than the electrophoretic velocity. If a DNA strand is at a location in a reservoir that is farther than this distance, L, from the nanopore, then the ensemble average of the molecule's motion due to drift and diffusion is away from the nanopore rather than toward the nanopore. If the molecule is at a location in a reservoir that is closer to the nanopore than the distance, L, then the ensemble average of the molecule's motion is toward the nanopore.

Thus, based on this model, the stronger the electric field that is provided in the reservoirs, the larger the reservoir volume within which a molecule can be occupied without being lost in the reservoir fluid bulk. The model above enables selection of required electric field and voltage application for a given molecule of interest and reservoir configuration. The upper limits on applied field strength are set by the electrical breakdown voltage of the structure in which a nanopore is provided, by the current saturation in the control circuit, and by the temporal resolution of the translocation detection technique, as higher-speed translocations, driven by higher electric fields, require higher-speed current measurements. This model provides one example of a technique for determining requisite molecular driving forces for a selected molecule, for a nanopore configuration, and for reservoir conditions, to achieve molecular capture and recapture events.

Referring back to FIG. 3, with a selected driving force implementation, a corresponding nanopore translocation detection technique is employed to detect molecular interaction with the nanopore and to control the timing of change in directionality of an applied force on a molecule back to the nanopore for a further capture event. In the example implementation described above and also shown in FIG. 3, electrical current flow is monitored to detect a blockage in ionic current flow through the nanopore by a molecule 10. Here a detection circuit 26 provides a current monitoring element, I, or other element, for monitoring ionic current, and a feedback controller 28 connected to adjust the magnitude and polarity of a voltage source, V, for applying a voltage in response to detected changes in ionic current.

The invention is not limited to nanopore translocation detection by ionic current measurement. Nanopore translocation by a molecule can also be detected by, e.g., transverse current measurements, such as measurement of electron flow across the nanopore, or measurement of current tunneling through a molecule at a nanopore, both monitored by electrodes sited at the nanopore. Detection of nanopore translocation can also be accomplished by, e.g., measurement of capacitance modulation, by optical detection, or by other selected detection technique. Additional transport properties that can be measured as a molecule traverses a nanopore include capacitance, conductance, resistance, charge, concentration, e.g., a number of monomers along a molecular length, optical properties for, e.g., fluorescence, such as by fluorescent labeling, and Raman scattering, such as by near-field Raman scattering, and chemical structure. Nanopore translation can further be detected by modulation of an electronic device, e.g., modulation of the conductance of an FET channel at the site of the nanopore. Further, an electrochemical sensor or other sensing element can be provided adjacent the nanopore for detecting molecular interaction with the nanopore. The invention is not limited to a particular translocation detection technique.

For clarity of discussion, one example detection technique, namely, ionic current blockage measurement, is discussed herein in detail, but it is to be clear that the invention is not limited to such. A range of suitable methods and device arrangements for detecting current and other parameters in a nanopore system can be implemented in the manner described, for example, in U.S. Pat. No. 6,746,594, issued Jun. 8, 2004; U.S. Pat. No. 6,673,615, issued Jan. 6, 2004; U.S. Pat. No. 6,627,067, issued Sep. 30, 2003; U.S. Pat. No. 6,464,842, issued Oct. 15, 2002, U.S. Pat. No. 6,362,002, issued Mar. 26, 2002; U.S. Pat. No. 6,267,872, issued Jul. 31, 2001; U.S. Pat. No. 6,015,714, issued Jan. 18, 2000; U.S. Pat. No. 5,795,782, issued Aug. 18, 1998, U.S. Publication No. 2004/0121525, published Jun. 24, 2004; U.S. Publication No. 2003/0104428, published Jun. 5, 2003, and U.S. Publication No. 2008/0171316, published Jun. 17, 2008; the entirety of each of which is hereby incorporated by reference.

Turning now to conditions of the reservoirs of the molecular capture system, such as the cis and trans reservoirs 12, 16, in FIG. 3, the fluids in the reservoirs can be the same or different. The reservoir fluids can be electrically conducting or non-conducting and can include a range of species for interaction with a molecule of interest. If the reservoirs are provided with differing environments, the segregation of those environments by the nanopore and its supporting structure enables the selected exposure of a molecule to the environments by controlled nanopore translocation between the environments. Thus, the molecular capture and recapture processes of the invention can be employed to control interaction of a molecule with fluidic environments to determine, e.g., the effect of a change in fluid characteristics on the molecule. For example, changes in the nanopore translocation characteristics by a molecule as a function of transport between differing fluidic media can be employed to provide information on the presence, absence, or kinetics of intramolecular or intermolecular interactions. Specifically, because the translocation duration is directly impacted by the configuration of a molecule, a non-equilibrium configuration of a molecule produced by a difference between the cis and trans reservoir conditions can be distinctly identified by a deviation in translocation duration, a difference in ionic current blockage, a modulation of another detection mechanism, such as tunneling measurement or optical detection, or all of these.

In accordance with the invention, in one example embodiment, the cis and trans reservoirs are provided with fluids having differences in pH. For example, the cis reservoir can be provided with a fluid of a relatively low pH and the trans reservoir provided with a fluid having a pH sufficient to denature a dsDNA molecule. With this configuration, the DNA molecule translocates the nanopore a first time as a double-stranded molecule, and is recaptured at the nanopore as a single-stranded molecule. The time required for the denaturation of the molecule can be directly measured by controlling the timing of recapture at the nanopore in concert with precise detection of each translocation event.

The cis and trans reservoirs can also be provided with fluids having differences in the concentrations of selected solvents, solutes, or ions, e.g., to cause a change in the osmolarity or ionic strength of the fluid. The two reservoir fluids can also be distinguished by, e.g., a difference in the identity of a solvent, the identity of a solute, e.g., a change in an ion of a given electric charge, or the presence or absence of a solute. The energy applied to the fluid in each reservoir can also be distinctly controlled, e.g., by controlling temperature, magnetic or electric field, mechanical agitation, sonic energy, optical energy, or other energy application to the reservoir fluid. The fluids in the two reservoirs can also differ in viscosity.

In one example embodiment, the trans reservoir is provided with a selected reactive species in fluid. When a molecule under analysis provided in the cis reservoir translocates the nanopore to the trans reservoir, a reaction between the molecule and the species is initiated. The reaction can then be terminated by causing the molecule under analysis to translocate back to the cis reservoir. Controlled translocation of the molecule under analysis between the cis and trans reservoirs thereby enables controlled reaction and analysis of characteristics of the molecule at intermediate points during the reaction based on the detected translocation duration or ionic current blockage at each translocation event.

Such controlled reaction between a molecule under analysis and an interacting species can be provided as, e.g., binding between a nucleic acid and a complementary nucleic acid, a protein, an intercalcating compound, an alkylating agent, or other species. Similar interactions between such compounds and proteins and other molecules can also be studied. In a similar fashion, the ability of a species provided in one reservoir to encourage or inhibit a particular intramolecular or intermolecular event in the other reservoir can be determined. For example, the ability of chaperones to affect the folding of a polymer, e.g., a protein or nucleic acid, can be determined.

It is noted that such an interaction may prevent a molecule under analysis from being recaptured, e.g., because the molecule has been degraded or combined with another species so as to no longer fit within the nanopore. If an interaction by a molecule is expected to hinder or prevent its ability to traverse back through the nanopore under given flow conditions, the strength of the molecular driving force can be increased until the molecule is caused to traverse the pore. Measurements in such experiments can be used to determine the strength of interactions within a molecule or between it and other species.

Selected differences between the fluids in the cis and trans reservoirs can also be employed to determine, e.g., whether the pH, ionic strength, temperature, or other characteristic of a fluid had a direct impact on an intermolecular or intramolecular event. For example, the presence, absence, or kinetics of an intermolecular folding event can be determined as a function of the properties of a fluid in one of the reservoirs, based on translocation characteristics before and after exposure to the fluid.

Other changes to a molecule that can result from intermolecular interaction can also be studied. For example, a chemical species, e.g., drugs, ions, oliogomers, surfactants, nucleotide probes and primers, cofactors, enzyme substrates, and other species, can be provided in the trans reservoir for interaction with a molecule under analysis after translocation to the trans reservoir. Recapture of the molecule by the nanopore one or more times is then conducted to detect changes in translocation duration or other characteristic that can indicate a change in the molecule caused by exposure to the species in the trans reservoir. For example, binding, hybridization, pairing, denaturation, cleavage, chemical reaction or permutation, stabilization of a particular conformation, or other induced conformation change can be indicated by deviations in translocation duration or other characteristic. Such studies can be employed in accordance with the invention, e.g., drug discovery, for example, by assaying for candidate binding compounds and proteomics.

Further in accordance with the invention there can be provided differing media between the two reservoirs. For example, a gel can be provided in one of the reservoirs. With a gel in place, e.g., in the trans reservoir, interaction of a molecule with the gel can be controlled, e.g., to carry out electrophoresis or other selected technique.

In addition to these example analyses that are enabled by differing cis and trans reservoir characteristics, the molecular capture and recapture sequence of the invention provides distinct advantages and enables a wide range of analyses for both common and distinct reservoir fluids and configurations. For example, the capture and recapture process provides confirmation on a real-time, single-molecule, single-signal basis that an observed electronic signal is the result of a single molecule translocation. A molecule cannot translocate back through a nanopore if that molecule did not go through the nanopore in the first place, and so each recaptured molecule is shown unequivocally to have passed through a nanopore (twice), and the detected translocation current signals are therefore verified to correspond to passages of that molecule through the nanopore. Without such verification, statistical or chemical examination of thousands or millions of presumed translocations would be conventionally required. Therefore, multiple translocation measurements as a molecule translocates a nanopore multiple times can be employed to reduce errors in a measurement and further to correct for measurement signal noise. For example, data from multiple capture and recapture events can be employed to distinguish signals produced by molecular translocation from background noise on a single molecule basis. This technique is valid even for polydisperse samples and analytes for which no sensitive assay like PCR exists.

Of particular note is the ability of the capture and recapture process to enable a large number of translocation measurements to be obtained in a short period of time for a single molecule under analysis. As explained in detail below, the delay between a capture event and a recapture event can be controlled by timing of a reversal of the driving force polarity. With this ability, many translocation measurements can be made under reasonable experimental conditions and times. These many measurements can be averaged or otherwise statistically analyzed for achieving a wide range of analysis results, e.g., to provide higher accuracy about a property of the molecule than could be achieved by a single measurement. For example, a large number of capture and recapture cycles can be employed to provide a more accurate measurement of a molecule's length, diameter, conformation, including the presence or absence of other molecules bound to the molecule, and the composition of the components, monomers, or other species making up the molecule. Repeated capture and recapture cycles thereby enable improvements in measurements of ionic current signals, increases in signal to noise ratios, and enable measurement and signal error correction, e.g., in application in which one or more devices are integrated with the nanopore. Such measurements are described, for example, in U.S. Pat. No. 6,746,594, issued Jun. 8, 2004; U.S. Pat. No. 6,673,615, issued Jan. 6, 2004; U.S. Pat. No. 6,627,067, issued Sep. 30, 2003; U.S. Pat. No. 6,464,842, issued Oct. 15, 2002; U.S. Pat. No. 6,362,002, issued Mar. 26, 2002; U.S. Pat. No. 6,267,872, issued Jul. 31, 2001; U.S. Pat. No. 6,015,714, issued Jan. 18, 2000; U.S. Pat. No. 5,795,782, issued Jun. 10, 2004; U.S. Publication No. 2004/0121525, published Jun. 24, 2004; U.S. Publication No. 2003/0104428, published Jun. 5, 2003; and U.S. publication No. 2004/0110205, published Jun. 10, 2004, the entirety of each of which is hereby incorporated by reference.

Considering specifically example techniques for measuring the conformational dynamics of a molecule, a recapture and translocation back through a nanopore subsequent to an initial translocation can be employed to explore how a molecule's initial conformation is influenced by the translocation. For example, if a DNA strand is stretched or linearized by nanopore translocation from the cis reservoir to the trans reservoir, then upon recapture through the nanopore back to the cis reservoir the DNA strand translocation duration will be increased. Similarly, if a protein is linearized by nanopore translocation from the cis reservoir to the trans reservoir, then upon recapture through the nanopore back to the cis reservoir the protein translocation duration will be increased; if the protein is folded, then upon recapture through the nanopore back to the cis reservoir the protein translocation duration will be decreased. If a protein is stretched or linearized by nanopore translocation from the cis reservoir to the trans reservoir, then upon recapture through the nanopore back to the cis reservoir, the protein translocation duration will be decreased.

In a similar application provided by the invention, variations in a DNA molecule's structure that result in a defect due, e.g., to a particular sequence, to base mismatch, adhesion of a protein, or damage to the backbone, could result in an increase in a propensity for the molecule to bend at the defect site. This bending can be detected and measured by repeated capture and recapture of the molecule.

With these examples, it is demonstrated that the molecular capture and recapture system of the invention can be customized for a selected molecular experiment or analysis with reservoir conditions that provide environments of interest for the analysis. The molecular capture and recapture sequence is controlled in accordance with the invention to control the initiation and duration of exposure of a molecule to the reservoir conditions. The nanopore translocation that occurs for each molecular capture and recapture event in turn provides detection and measurement of molecular characteristics that result from exposure to the reservoir conditions. The molecular capture and recapture system thereby provides both nanoscale experimental environment and a molecular detection configuration for that environment.

The molecular capture and recapture system of the invention can further be controlled to form a sub-micron scale, single molecule trap. By continuously translocating a molecule back and forth through a nanopore the molecule is spatially trapped in the vicinity of the nanopore and can be transferred back and forth through the nanopore to a selected reservoir as-desired. The detection of ionic current blockage, or other selected parameter corresponding to nanopore translocation by the molecule, reveals the position of the molecule within the trap, and with triggered voltage or other driving force polarity reversals, provides a feedback mechanism to maintain the molecular trap conditions. This enables detection and characterization of a trapped molecule without the need for chemical modification.

A molecule that is trapped in the capture and recapture system of the invention can be maintained in the system for an extended period of time for a desired experiment or analysis. For example, during an extended trap duration, a characteristic in one of the reservoirs can be slowly changed over time and a molecule's response to the slow change measured. Changes include, e.g., temperature, pH, ion concentration, or other characteristic of one of the reservoirs.

The molecular capture and recapture system of the invention also provides distinct and important advantages as a DNA sequencing tool. In general, the compelling advantage of nanopore sequencing is the prospect of inexpensive sample preparation, requiring minimal chemistries or enzyme-dependent amplification. Thus, the cost of nanopore sequencing, by direct strand sequencing or other technique, is projected to be far lower than ensemble sequencing by, e.g., the Sanger method or by a massively parallel approach. Unlike these approaches, nanopore sequencing does not require the use of expensive purified fluorescent reagents, polymerases or ligases, and requires only unamplified genomic DNA, eliminating the cost of expensive enzymes, cloning, or amplification steps. Furthermore, nanopore sequencing can enable the sequencing of very long DNA fragments of, e.g., 5,000-50,000 nucleotides in length, which, compared to shorter fragments, can greatly simplify the assembly of multiple sequence reads and reduce the cost and well known inadequacies of the assembly process.

But like conventional DNA sequencing methods, nanopore sequencing is understood to also generally require six-fold or greater depth of coverage, i.e., to require a reading of each region of a genome at least six times, to produce a useable draft of a genome's sequence. Assuming a diploid human genome draft is desired, and that the genome is fragmented into 50,000 nucleotide fragments, then there would be approximately 120,000 such fragments the sequence of which must be read. Poisson distribution calculations predict that to assure >99.9% of the genome will be read 6 times or more, a mixture containing the 120,000 fragments derived from multiple copies of the target genome, i.e., an extract from multiple cells, should be analyzed with an 18-fold depth of coverage. This corresponds to reading about two million individual fragments.

Thus, there is central importance in an ability to conduct long sequence reads and to overcome the limitations of conventional nanopore sequencing systems for translating >50,000 nucleotide-long fragments. Such limitations are the result of a dependence of nanopore capture rates on a solution molarity, i.e., the concentration of fragment ends to be sequenced. Very high throughput translocation of short, single-stranded oligomers, e.g., <50 nucleotides, is easily achieved, and for these short molecules the measured concentration-normalized capture rate constant is ~5.8 oligomers (sec $\mu M$)$^{-1}$. But solutions of 50,000 nucleotide-long polymers are very viscous at the micro-molar concentrations usually used for short oligomers. Thus a solution of long oligomers provided for translocation through a nanopore must be held at a relatively low nano-molar concentration to avoid an excessive viscosity, which would inhibit mixing and molecular diffusion. Such a low nano-molar solution concentration containing 50,000 nucleotide fragments results in only a few of the molecules, perhaps only 1-2 every 5-10 sec, being captured by a nanopore per unit time even if the capture rate constants for 50,000 nucleotide-long and 50 nucleotide-long fragments are identical. Given the large number of fragments that must be read, it is therefore critical to minimize the dead time between one fragment having been translocated through a nanopore and the capture of the next molecule.

The molecular capture and recapture system of the invention overcomes this limitation to provide an efficient and time saving method that can achieve six-fold or greater coverage of 50,000 nucleotide-long oligomers. First, by precisely controlling the molecular driving force that causes a molecule to be recaptured after an initial nanopore translocation, a molecule can be recaptured by, e.g., reversing the voltage bias between the reservoirs, within one or two milliseconds after the molecule has translocated the nanopore. Because a 10,000-50,000 nucleotide-long molecule cannot in such a short time diffuse out of the hemispherical electrical field near the nanopore, and because the molecule begins translocation almost immediately upon its return to the nanopore, the deadtime between capture and recapture at the nanopore is two to three orders of magnitude less than the dead time between sequential capture events of a series of molecules each translocating only once through a nanopore.

Thus each 50,000 nucleotide fragment captured by the nanopore can in accordance with the invention be recaptured and re-read a selected number of times, e.g., 6 or more times, assuming 6-fold coverage is required, before purposely being discarded in the trans chamber. The molecular capture and recapture system of the invention thereby enables the repeated analysis of a selected nucleotide fragment a selected number of times by a capture-recapture sequence, and followed by a repeated analysis of a next nucleotide fragment, until all nucleotide fragments in a solution under study have been analyzed in accordance with a required depth of coverage.

Further, rather than requiring an assurance that >99.9% of a genome will be read a required number of times, e.g., 6 times or more, by random sampling of fragments in the conventional manner, i.e., by capturing and reading each captured fragment only once, the molecular capture and recapture system of the invention enables the use of real-time software or other diagnostic system to distinguish a previously read fragment from an unread fragment during a first passage of that fragment through the nanopore. In this configuration, the detection signal from each translocation event is compared with a database of collected signals to identify an unread fragment. If an unread fragment is positively identified, then that fragment is recaptured a selected number of times for re-analysis to assure the desired fold coverage. If a fragment is identified as having already been read, then the molecular driving force is controlled to discard the read fragment into the bulk solution of the trans reservoir rather than being recaptured to the cis reservoir.

As a result, in this configuration, only previously unread fragments are recaptured and read the requisite number of times, e.g., six or more times, and the previously read fragments are discarded into the trans chamber after the initial translocation needed to determine whether or not a fragment had previously been read. This technique provided by the invention avoids the 18-fold coverage depth needed to assure that >99.9% of a genome is read 6 or more times.

The real-time analysis of molecular translocation data that is enabled by the molecular capture and recapture system of the invention provides a wide range of additional methods. For example, regardless of the sequencing method, it is well known that certain sequences in the genome are more difficult to read, and produce a lower quality read-out, than other sequences in general. In accordance with the invention, if an initial number of molecular fragment translocations, e.g., 6 or more translocations, of an individual nucleotide fragment is determined by real-time software to have produced an incomplete or a poor-quality read-out, the recapture system can be controlled to promptly recapture that fragment to be re-sequenced a number of additional times as-required to produce a desired read-accuracy. This technique of the invention eliminates the conventional requirement to re-sample an entire genome to randomly chance upon a particular hard-to-read fragment of the genome.

These examples demonstrate that the molecular capture and recapture system of the invention can be implemented with data analysis capabilities to select a nucleotide fragment to be sequenced and the number of times that fragment is sequenced. With real-time data analysis, the system can be controlled to initiate and continue a molecule's analysis, to terminate a molecule's analysis, or to re-initiate a molecule's analysis. The time scale of molecular capture and translocation enabled by the system is elegantly exploited here as it corresponds to the speed of real-time data analysis. Genomic sequencing can therefore be accomplished by molecular capture and recapture in accordance with the invention in a manner that overcomes the significant limitations associated with conventional single-capture nanopore sequencing.

Turning now to other aspects of the invention, there can be provided adaptations of and companion components to a molecule of interest to enhance the efficiency with which that molecule is captured or recaptured. For example, because recapture efficiency is in general diminished when an oligomer diffuses out of the hemispherical electrical field near the nanopore, it can be preferred for some applications to adapt the molecular structure to enhance the recapture efficiency for that molecule.

Figure 4A:
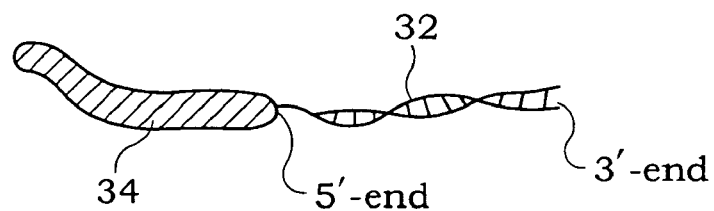
FIGS. 4A-4B are schematic views of example species that can be provided with DNA molecules in accordance with the invention for capture and recapture analyses of the DNA molecules.
Figure 4B:
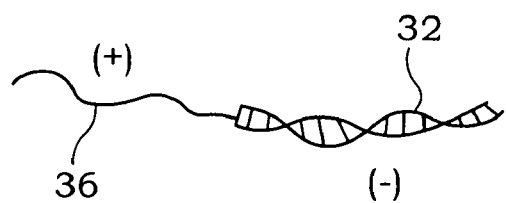

In one example technique, the molecule is adapted so that the speed of the molecule is reduced as the molecule is about to exit from the nanopore. By reducing the speed of a translocating molecule, the length of time the molecule resides within the hemispherical recapture field before diffusing into the bulk solution is increased. Referring to FIG. 4A, in an example configuration, there can be attached to, e.g., the 5'-end of a DNA strand 32, chemical groups or molecules 34 of greater diameter than the DNA strand itself but of sufficiently small diameter to translocate the nanopore. Referring to FIG. 4B, there further or alternatively can be attached chemical groups or molecules 36 having an electrical charge opposite to that of the DNA molecule 32, e.g., having a positive electrical charge in opposition to the negatively-charged DNA backbone. Because the attached groups interact with the side-walls of the nanopore due to their extended diameter, or are positively charged in opposition to the molecular driving force, the groups attached to the DNA strand of interest translocate the nanopore at a much slower rate than the DNA strand itself. As a result, the overall translocation speed is reduced, and the length of time the DNA strand resides within the hemispherical recapture field before diffusing into the bulk solution is increased. The attachment of such groups can preferably be at the 5'-end of a DNA strand because it is known that the 3'-end of DNA is more likely to be captured by a nanopore than the 5'-end.

Further, such an attachment of a group having an opposite electrical charge or a diameter greater than that of the DNA strand itself, when located at the 5'-end of the DNA strand, greatly reduces the probability that the DNA molecule will initially be captured and traverse the nanopore from the 5'-end to the 3'-end. Indeed, after a first nanopore translocation, the DNA molecule is unlikely to be re-captured and translocate from the 3'-end to the 5'-end only if the voltage bias across the nanopore, between the reservoirs, is reversed soon enough that the 5'-end of the molecule is still dawdling inside the nanopore. If the molecule and its extension has fully exited from the nanopore, recapture will most likely translocate the molecule again through the nanopore from the 3'-end to the 5'-end.

In a further configuration provided by the invention, there can alternatively be attached to the 5'-end of a DNA strand chemical groups or molecules of greater diameter than the DNA strand, as in FIG. 4B, and indeed of greater diameter than the nanopore itself. This condition guarantees that only the 3'-end of the DNA molecule is initially captured, and therefore that the first nanopore translocation is from the 3'-end to the 5'-end. This condition also guarantees that the DNA molecule is never released from the nanopore into the trans reservoir. After an initial translocation, upon voltage bias reversal, the DNA strand translocates back through the nanopore from the 5'-end to the 3'-end and is released into the cis reservoir. Because the 3'-end of the molecule would be the last to escape from the nanopore into the cis reservoir, this 3' end—which is inherently more likely to be captured by a nanopore than the 5' end—would be closest to the nanopore immediately after release. Thus, attaching chemical groups or molecules of greater diameter than the nanopore to the 5'-end of the DNA strand guarantees that molecules are never be lost in the trans reservoir, and diminishes the probability of molecular loss in the cis reservoir because the molecule is released in the cis reservoir in an orientation most favorable for recapture from the cis reservoir.

This configuration can be extended to an arrangement in which a molecule to be attached to a DNA strand is also attached to a structure adjacent to the nanopore, e.g., in the cis reservoir. For example, a complementary strand can be provided on the surface of a membrane in which the nanopore is formed, and hybridized with the DNA strand. The DNA strand can translocate the nanopore in both the forward and reverse directions, but is effectively tethered in the cis reservoir such that the strand cannot escape from the vicinity of the nanopore.

With these examples, it is demonstrated that in accordance with the invention, selected species can be provided as a companion to a molecule to be captured such that the capture, translocation, and recapture characteristics of the molecule are controlled. No specific species to be provided is required by the invention; all that is required is the attachment or other interaction of a selected species with the molecule in accordance with characteristics of molecular translocation under consideration. This technique therefore provides additional degrees of control in aspects of molecular translocation and recapture.

Referring now to FIG. 5, there is shown an example implementation of a control system 40 provided by the invention for controlling the capture, translocation, and recapture of a molecule through a nanopore as in FIGS. 1-3. As shown in the figure, the nanopore is configured for connection between reservoirs, e.g., with a PEEK flow cell 42. With the feedback control circuit 26 shown in FIG. 3, there is provided a detected current, I, that is provided to a measurement device, e.g., a current amplifier 44, such as an Axopatch 200B amplifier, from Molecular Devices, Corp. The amplifier measures an electrical current, I, corresponding to the nanopore ionic current flow, and applies between the reservoirs a bias voltage, $V_{nanopore-cell}$, that is set by the feedback controller, as described below. The measured current, I, is then processed by a high-pass filter 46. This highpass filter removes the DC baseline current level. As a result, when the baseline current is positive, the filter output pulse is negative, and when the baseline is negative, the filter output pulse is positive. For a molecular capture event in a capture and recapture sequence, the filter's settling time in response to a step should be minimized and such can be accomplished by, e.g., a simple RC filter. In addition, the amplifier output can be passed through an absolute value circuit to eliminate the large step observed when the current switches from +I to −I.

The filtered output signal is accepted for feedback trigger generation to reverse the polarity of an applied molecular driving force by a controller 48, e.g., by programmed analog circuitry on a PXI-6070E DAQ card, from National Instruments, Inc. The controller 48 is programmed with a selected current comparator threshold, with a selected trigger delay, and with voltage control. The controller 48 produces a feedback control voltage, $V_{CONTROL}$, that is sent to the amplifier 44 to impose the corresponding voltage bias at the flow cell 42, across the nanopore between the cis and trans reservoirs.

For a capture event in a molecular capture and recapture sequence, a comparator can be employed to trigger a pulse generator implemented with counters on the PXI-6070E card, to produce a change in voltage. For a recapture event in a molecular capture and recapture sequence, the bandpassed signal is directed to a comparator used to trigger the programmed output of an analog waveform to control the reservoir bias voltage. The controller also sends the control voltage to a data acquisition system, e.g., a Digidata 1322A, from Molecular Devices Corp., to record the voltage control signals at a hard drive along with the filtered current signal measurement.

Figure 6:
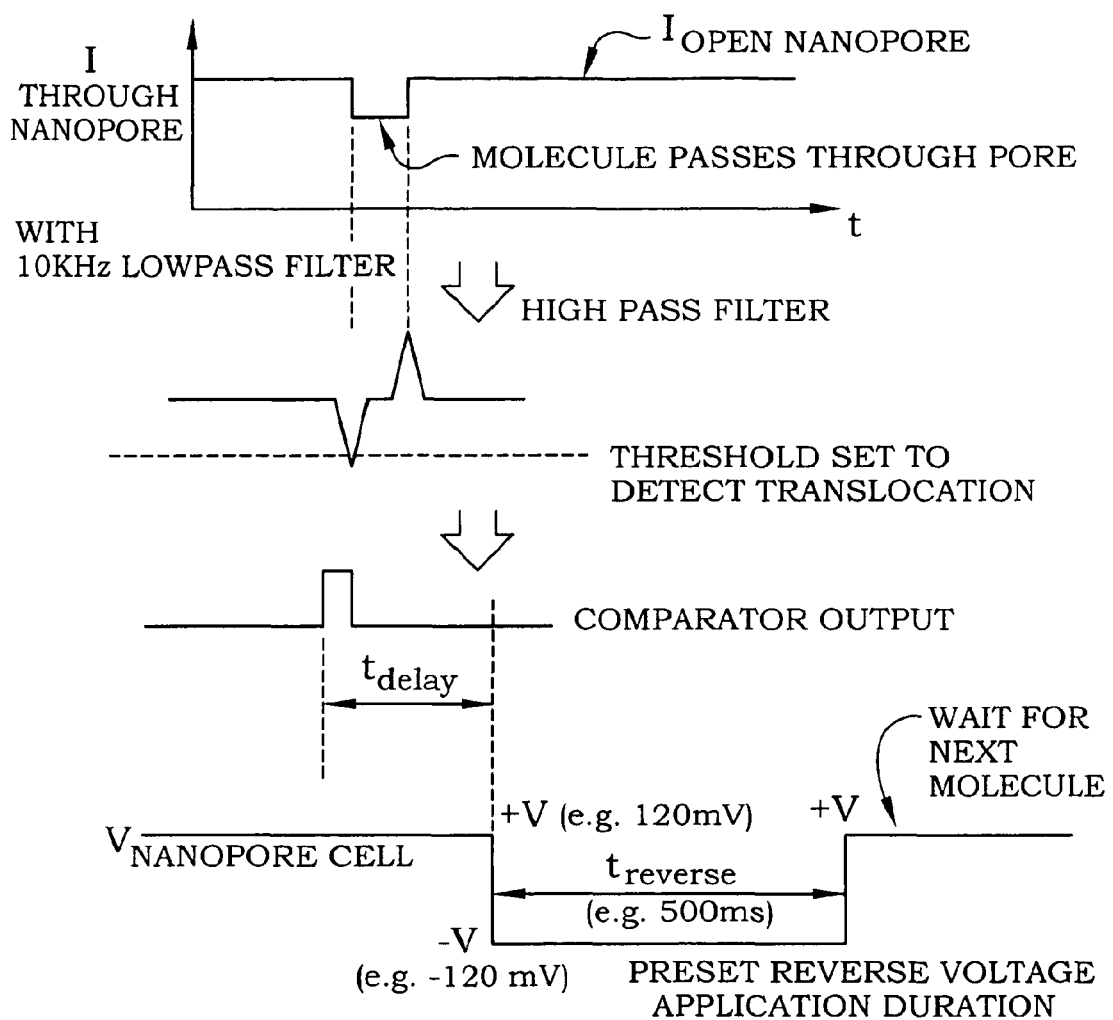
FIG. 6 is a timing diagram of an example control sequence for operating the feedback control loop of FIG. 5.

A timing diagram illustrating an example molecular capture and recapture cycle enabled by this system is shown in FIG. 6. When a molecule translocates the nanopore from the cis reservoir to the trans reservoir, the measured current, I, is reduced during the translocation and the current reduction produces a negative highpass filter pulse at the start of the translocation and a positive pulse at the end of the translocation. The delay period, $t_{delay}$ imposed prior to the reversal of the applied voltage bias polarity, can be initiated at the detection of the start of the translocation event or the detection of the end of the translocation event. In the example of FIG. 6, the delay is initiated at the start of the translocation event. As explained below, the delay period can be held constant or varied for a given capture and recapture sequence. At the end of the delay period, the bias voltage at the nanopore cell, $V_{nanopore\ cell}$, is reversed in polarity. For many applications, it can be suitable to impose this reverse-polarity bias for a preset duration, $t_{reverse}$, known to be sufficient to recapture the molecule to translocate the molecule back to the cis reservoir. At the end of this recapture duration, the bias voltage at the nanopore cell, $V_{nanopore\ cell}$, is again reversed in polarity, and the system awaits detection of a molecule translocation from the cis reservoir to the trans reservoir.

The delay period, $t_{delay}$, imposed prior to the reversal of the applied voltage bias polarity, can be set based on considerations of system operation and for a given molecular analysis. Considering first if the molecular driving force field were turned off immediately after a molecule passed through the nanopore, rather than reversed, then the time, on average, for the molecule to diffuse a distance L away from the nanopore would be $L^2/D$, where D is the diffusion constant, as described above. Now given that the molecular driving force field is not turned off after a molecule translocates the nanopore and instead directs the molecule away from the nanopore during the delay period, the actual time to reach this threshold is less. Thus, if desired, in accordance with the invention the voltage can be turned off as soon as a molecule translocates the nanopore, if desired to retain the molecule in the hemisphere of capture for a longer duration, but here the triggering and detection system can be more complicated, and less preferable, in that the system must be triggered on a detection of a molecule leaving the nanopore, not entering it. Thus, for many applications it can be preferred to impose some delay period prior to molecular driving force polarity reversal.

In general, it can be preferred that the delay period, $t_{delay}$, be much less than the time it characteristically takes a molecule to reach the outermost trap distance, L, as given above, moving outward, to retain the molecule for additional translocation. Ignoring diffusion, this time can be calculated from the differential equation $$dr/dt = \frac{|\mu I|}{2\pi \sigma r^2} \text{ or } r^3 = \frac{3|\mu I|}{2\pi \sigma}t,$$

so $$t(L) = \left(\frac{|\mu I|}{2\pi \sigma D}\right)^3 \frac{2\pi \sigma}{3|\mu I|} = \frac{|\mu I|^2}{12\pi^2 \sigma^2 D^3}.$$

For an example of a 4 kb DNA strand, this value is 130 ms. With diffusion, ignoring the drift term, the time $L^2/D$ is ~400 ms. In practice, the results from experimental analysis and from numerical calculations show that a few ms delay can be the preferred maximum delay to enable efficient recapture so that recapture with near unit efficiency, i.e., even the tails of the probability distributions of molecules that diffuse rapidly away from the nanopore, can be recaptured. For an increase in current, due, e.g., to an increase in applied voltage, the delay period can be extended. For some applications, a maximum delay time of 10's of ms can be preferred, e.g., less than 100 ms, so long as that delay time is much less than the characteristic time required for a molecule to reach the outermost capture distance, L.

The minimum acceptable delay period for a given application can be determined by considerations for complete detection of a molecule passing through the nanopore. For some duration, e.g., ~<100 s of microseconds, after the applied voltage bias is reversed, the nanopore structure, e.g., a membrane, capacitively charges, drawing excess current. During this time, molecular translocation events cannot be detected. Although this current can be provided in parallel to the feedback circuit with the Axopatch 200B's capacitance compensation circuitry, at the edge of the transition, ~50 microseconds or so, translocation detection is not possible. Thus, the triggering circuitry for many implementations must be provided with a characteristic reset time, e.g., associated with the high pass step response, that must be allowed to pass before the molecule can re-translocate the nanopore. Also, given a feedback control paradigm that triggers recapture based on the detection of the initiation of a translocation event, then the delay period, $t_{delay}$, must be long enough to accommodate complete translocation by the molecule before the voltage is reversed; the delay is limited by the uncertainty in translocation duration. Finally, if it is desired to maximize the total molecular trap time, then the delay between translocations should be maximized, because each translocation carries a risk that the molecule will behave unexpectedly and somehow become lost from the trap. Based on these considerations, a minimum value of the delay period, $t_{delay}$, is thus preferably between about 0.5 ms and about 1 ms.

If desired for a given application, the molecular capture and recapture system can be controlled to ensure that voltage application is reset if a molecule is lost from the vicinity of a nanopore after translocating through the nanopore, or is transformed in some way such that the molecule does not return through the nanopore. To obtain such a reset control, a counter can be implemented to count the number of voltage polarity reversals, which indicate molecular translocation events. If the counter does not increment during a prespecified duration, e.g., between about 200 ms and about 1000 ms, then it is known that the molecule is lost from the system and should be reset by switching the polarity of the voltage back to its previous state. This enables sequential capture and recapture cycles to be continued even after a molecule is lost from the vicinity of a nanopore.

The control timing sequence shown in the timing diagram of FIG. 6 is only one example in a wide range of control timing techniques that can be implemented in accordance with the invention for molecular capture and recapture. For example, in one alternative technique, there is determined a threshold voltage, $V_{THRESH}$, below which a molecule of interest is known to not translocate a nanopore unless the magnitude of an applied voltage, $V_{APPLIED}$, is greater than the threshold voltage, as in $|V_{APPLIED}|>V_{THRESH}$. Then a first applied voltage, $V_1$, is defined as $|V_1|>V_{THRESH}$, and a second applied voltage, $V_2$, is defined as $|V_2|<V_{THRESH}$.

With these voltage selections, a molecular capture-recapture cycle is initiated by first setting the applied nanopore bias as $V_{APPLIED}=+V_1$. This bias causes a first translocation event, e.g., from the cis reservoir to the trans reservoir. After detection of the molecule translocation, the applied voltage is then set as $V_{APPLIED}=-V_2$. This holds the molecule at the nanopore site without translocation back through the nanopore, spatially trapping the nanopore, e.g., in the trans reservoir, right at the nanopore. After a selected trap duration, the applied voltage is then set at $V_{APPLIED}=+V_2$ to move the molecule away from the nanopore so that the molecular entry into the nanopore can be distinguished from the voltage transition due to nanopore structure charging, as explained above. Finally, the applied voltage is then set at $V_{APPLIED}=-V_1$, to cause translocation of the molecule through the nanopore back to the other reservoir. This example control timing scenario demonstrates that the molecular capture and recapture cycle of the invention can be adapted for a variety of molecular events and is not limited to a particular control and measurement sequence. All that is required is the adjustment of the molecular driving force at one or more times during a control sequence to cause molecular translocation of the nanopore at least one time in both a forward and a reverse direction.

Turning to example nanopore structures for enabling a selected molecular control sequence, as explained above, in accordance with the invention the nanopore is preferably provided in a support structure that accommodates a nanoscale diameter for the nanopore and that accommodates no more than a microscale length for the nanopore. As explained above, the length of the nanopore, between surfaces of a support structure, sets the general thickness of the structure separating the two reservoirs. The support structure can become capacitively charged as a voltage bias is switched in polarity between the two reservoirs. A smaller area of support structure in contact with the fluid results in a lesser capacitive charging and faster control and detection triggering. A small area support structure can therefore be preferred for most applications.

A microelectronic membrane is particularly well-suited as a nanopore support structure. The membrane can be provided as, e.g., a nitride, such as $SiN_x$, an oxide, or other insulating structure that achieves electrical insulation between the two reservoirs, particularly for applications in which fluids provided to the reservoirs are electrically conducting, as in the case of ionic fluids and electrically charged molecules such as DNA. The membrane can be formed of multiple materials, of composite materials, or other selected arrangement that enables a selected detection and triggering control scheme.

A nanopore can be formed in a selected solid state support structure by any convenient process, e.g., by ion beam milling, electron beam milling, ion beam sculpting, wet or dry etching, or other selected process. The support structure for the nanopore, as well as electrical probes, sensors, contact pads, electronic devices, or other structures, can be fabricated in any suitable manner as-desired for a given molecular analysis application. Fabrication processes for producing microelectronic membranes and for producing nanopores in such membranes with associated detection and electronic connections and probes can be implemented in a manner best-suited for a given application, as, e.g., in U.S. Pat. No. 6,783,643, issued Aug. 31, 2004; U.S. Pat. No. 6,627,067, issued Sep. 30, 2003; U.S. Pat. No. 7,258,838, issued Aug. 21, 2007; U.S. Pat. No. 6,464,842, issued Oct. 15, 2002; U.S. Publication No. 2004/0229386, published Nov. 18, 2004; U.S. Publication No. 2008/0171316, published Jul. 17, 2008; U.S. Publication No. 2005/0006224, published Jan. 13, 2005; U.S. Publication No. 2005/0241933, published Nov. 3, 2005; and U.S. Publication No. 2005/0126905, published Jun. 16, 2005; the entirety of all of which are hereby incorporated by reference.

The invention is not limited to solid state support structures and nanopores. Biological nanopores can be employed as-suitable for a given application. For example, the toxin produced by the bacterium *S. aureus* is a protein called α-hemolysin. Monomers of this protein in an aqueous solution self-assemble into lipid bilayers, or into cell membranes, as a heptamer that creates an aqueous channel or nanopore of diameter ~1.5 nm through the lipid bilayer.

The following examples are provided to describe measured results and data analysis achieved in accordance with the invention with experimental solid state nanopore systems and control techniques.

EXAMPLE I

Nanopores of about 6 nm in diameter were fabricated in a ~20 nm thick SiN membrane using a condensed transmission electron microscopy (TEM) beam. The unsupported area of the membrane had lateral dimensions greater than 20 microns, whereby the nanopore could effectively be represented as a hole in an infinite electrically insulating sheet. To reduce the capacitance of the system the SiN membrane was supported on a 2 µm-thick silicon dioxide layer, which was provided on a 3 mm silicon wafer having a pyramidal pit fabricated by standard MEMS bulk micromachining. With this configuration, the total capacitance of the silicon wafer, nanopore reservoir flow cell arrangement, and fluid inputs was measured to be 13 pF.

The membrane-nanopore configuration provided on the silicon wafer was assembled in a PEEK flow cell with PDMS gaskets. After assembly, the wafer configuration, the holder, and the gaskets were oxygen plasma cleaned for 60 s at 100 W and 500 mT. Immediately after the plasma cleaning, 1 M KCl solution with 10 mM TE buffer at pH 8 was added to the flow cell, and a baseline ionic current flow through the nanopore, between the two reservoirs, and through the measurement circuit, was established. Voltage was sourced and current measured using an Axopatch 200B amplifier in resistive feedback mode with a 4 pole low pass Bessel filter with a 10 kHz cutoff frequency. The amplifier output was digitized at 200 kHz and continuously recorded to disk using a Digidata 1322A digitizer and pClamp software.

An equimolar mixture of 6 kilobase-pair (kbp) and 4 kbp DNA fragments were obtained from New England Biolabs. The fragments were provided in TE buffer at a concentration of 0.5 mg/mL. 4 µL was diluted in 50 µL of the 1 M salt buffer, then almost the entire amount was slowly added to, and through, the 1-2 µL volume of the cis reservoir of the flow cell, which was contacted by the ground electrode. This ensured a repeatable concentration of DNA in the cis chamber.

A forward voltage of 120 mV was applied to the flow cell and controlled by a National Instruments DAQ card (PXI-6070E) and Labview software, from National Instruments, Inc. The amplified current signal was passed through a band-pass filter and used to trigger the voltage reversal. After a molecule was detected entering the pore, the forward voltage was maintained for a programmed delay period before a reverse voltage of −120 mV was applied. The lag introduced by the filters was comparable to the translocation time through the nanopore, of about 100-200 µs, whereby even though the reversal was triggered on the leading edge of a translocation detection, the delay could be considered as entirely after the molecule's translocation. Once the voltage was reversed, the voltage was maintained at −120 mV for 500 ms, then restored to +120 mV. The return to positive voltage was not triggered and took place 500 ms after the voltage was initially reversed, regardless of whether any molecules translocated during this interval.

Current blockage signals from individual molecular translocations can be characterized by the time duration of the blockage, the magnitude of the blockage, and by the integral of the current blockage over the length of the event. This last quantity, which is herein termed the event's area, or the event charge deficit (ecd), is the amount of additional charge that would have passed through the nanopore without the molecule blocking some of the ionic current. This ecd is independent of the conformation of the molecule, e.g., folded or unfolded, as the molecule translocates the nanopore and depends on the length of the molecule.

FIG. 7A is a histogram plot of ecds for all translocations measured in the forward direction, i.e., from the cis reservoir through the nanopore to the trans reservoir. This histogram is fit to the sum of two Gaussian distributions representing 4 kbp and 6 kbp free translocations—the dotted lines in the plot represent the two Gaussians whose sum was fitted to the histogram. Signals with large ecd, >30 pC, represent molecules that stuck to the nanopore wall at some point in the translocation and hence have longer translocation times. These are not included in the fit.

Based on these fit Gaussians and each signal's ecd, there was determined the likelihood that a given blockage corresponded to translocation of a 4 kbp molecule or a 6 kbp molecule in both forward and reverse translocation events. The signals from reverse translocations were sorted by whether the forward translocation that immediately preceded each reverse translocation was of a 4 kbp or 6 kbp molecule. FIG. 7B is a histogram plot of ecds for reverse translocations following 4 kbp and 6 kbp forward translocations. The plot shows ecd reverse translocations where the forward translocation of a molecular length was determined with 70% or greater probability to have preceded the reverse translocation with that length.

Comparing the forward and reverse translocation histograms of FIGS. 7A-7B, it is found that the length of a molecule translocating the nanopore in the reverse direction agrees with the length of the molecule that translocated the nanopore just previously in the forward direction. In other words, the length of each returning molecule was measured as being the same as the length of the molecule that had just translocated the nanopore, within the limits of the nanopore resolution. This demonstrated that the triggered voltage reversal recaptured the same molecule whose detected passage triggered that reversal.

For additional analysis, data from the experiment above was analyzed by identifying each molecular translocation signal as an "event," with each event labeled "forward" or "reverse" according to whether it occurred during a time when the voltage bias was positive or negative, respectively. In addition, each event was labeled by the time duration of its occurrence since the last transition in bias voltage. The events were binned into quantized time increments 50 ms wide, chosen by a compromise between time resolution and statistical accuracy. The experiment proceeded over many forward and reverse capture and recapture cycles and each bin was incremented by one event if the event occurred within the bin's time boundaries. The counting rate for each bin was then determined by dividing the total number of accumulated events in a bin by the total time during an experiment that the bin had been accessible. For reverse events that time is the bin time increment multiplied by the number of forward/reverse cycles. For forward translocation events the situation was more complex because each forward translocation event triggered a bias transition, thereby terminating the sampling of forward events that occurred at later times. This caused the effective length of a time bin to be foreshortened, depending on the delay time to the reverse transition, and it caused fewer cycles to be associated with events occurring long times after the positive voltage transition than for shorter times.

Figure 8B:
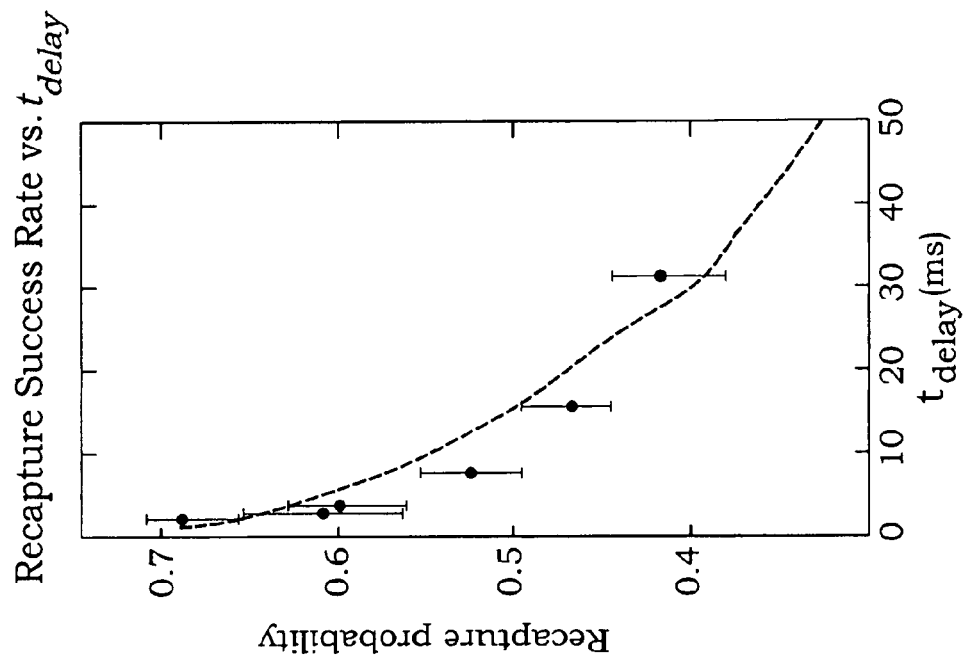
FIGS. 8A-8B are plots of the molecular capture rate and recapture probabilities, respectively, in an experimental molecular capture and recapture system in accordance with the invention.
Figure 8A:
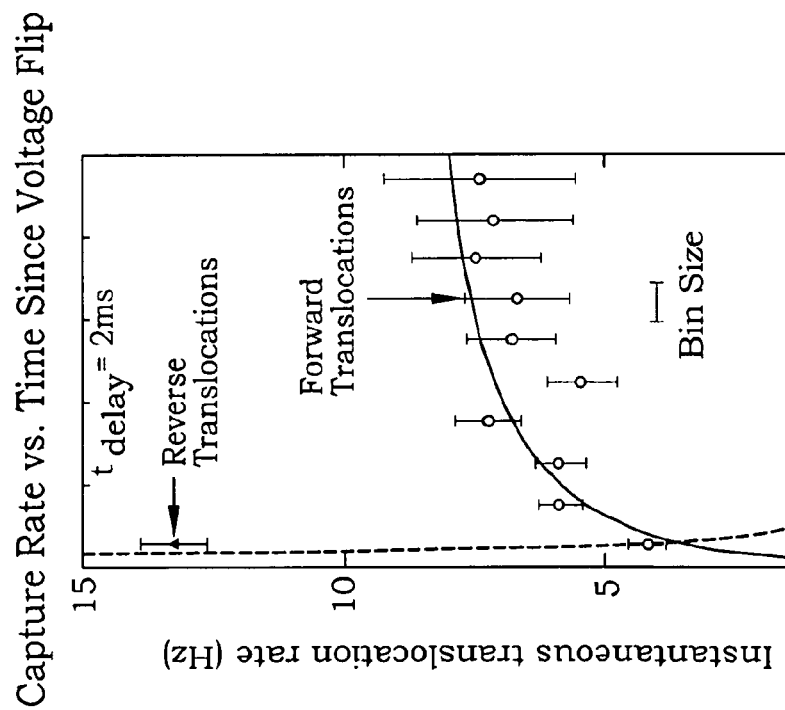
Figure 9D:
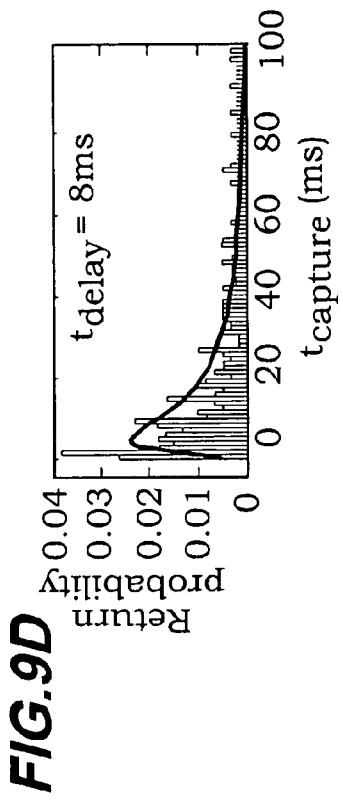
FIGS. 9A-9F are plots of capture time histograms for the recapture of a molecule at a nanopore for various delay periods, in an experimental molecular capture and recapture system in accordance with the invention.
Figure 9E:
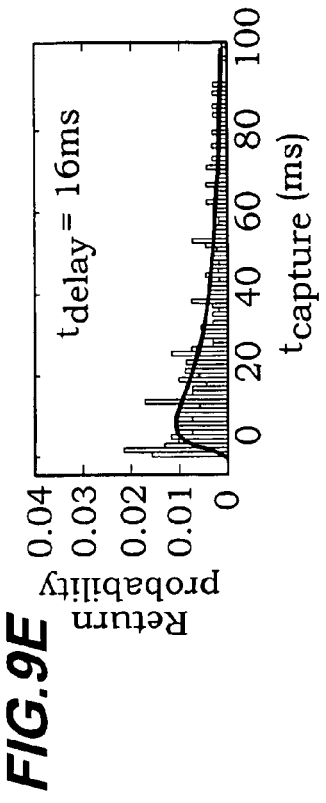
Figure 9F:
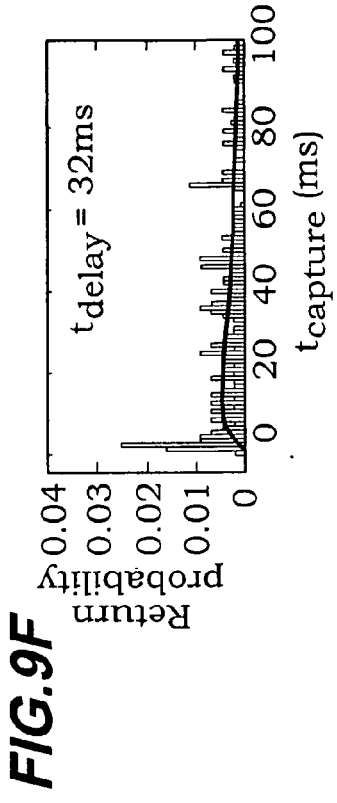
Figure 9A:
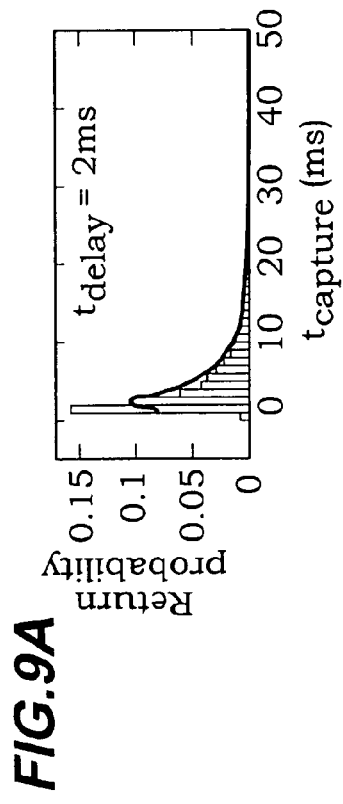
Figure 9B:
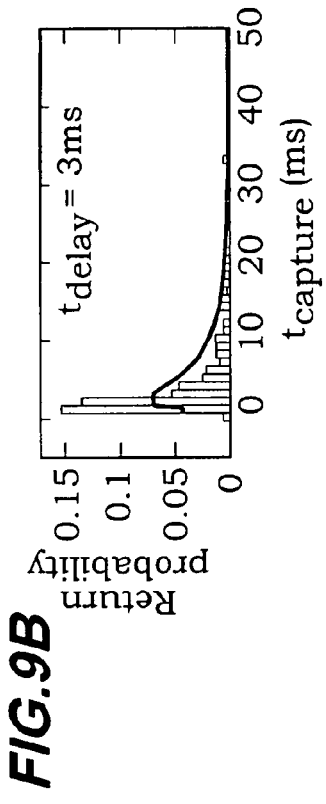
Figure 9C:
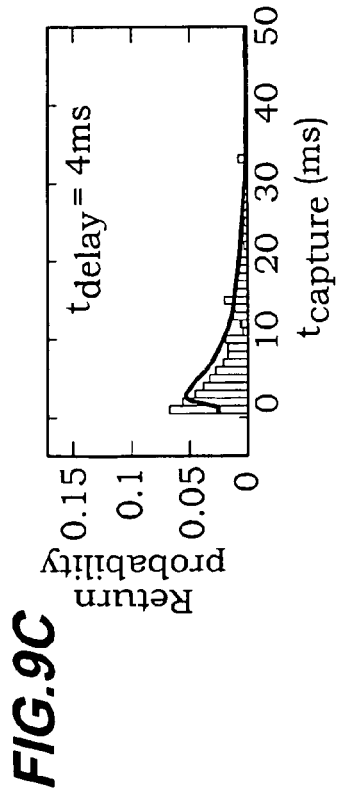

With this data analysis, FIG. 8A is a plot of instantaneous capture rate, i.e., the rate at which molecules arrived for translocation at a nanopore as a function of time since the previous voltage reversal. As stated above, the delay period for these translocation experiments was set at 2 ms. Each point in the graph represents the average rate at which molecules entered the nanopore during the surrounding 50 ms time interval. For example, the point at 25 ms represents the rate between 0 and 50 ms after the voltage polarity reversal, termed in the plot "voltage flip." The solid line, corresponding to forward-biased capture, and the dashed line, corresponding to reverse-biased recapture, represent predictions of a drift-diffusion model discussed below. In the plot, both of the binning data effects discussed above are accounted for.

The chance that a molecule will translocate the nanopore between time t and t+dt seconds after a switch in voltage bias polarity is r(t)dt. If the arrival of molecules at the nanopore was uncorrelated with that voltage polarity switch, then r(t) would be expected to be constant. But from the plot of FIG. 8A it is shown that r(t) is not constant in either direction. In the forward translocation direction for capture of molecules from the cis reservoir, the capture rate is suppressed shortly after the voltage is made positive. This is because the molecules in the cis reservoir had been previously driven away from the nanopore during the previous 500 ms of reverse-voltage polarity. In contrast, the recapture rate was greatly enhanced immediately after the molecular driving voltage was switched to negative polarity. This is because the switch to negative polarity was triggered by the previous translocation of a molecule through the nanopore, and thus that there was a molecule very near to the nanopore at the time the voltage was reversed.

The peak in the recapture rate shown in the data plot of FIG. 8A to have occurred immediately after the triggered voltage polarity reversal proves that the same molecule was being recaptured. It would be completely inconsistent with capture of a different molecule form the bulk solution of the trans reservoir. Also, if a voltage polarity reversal in and of itself were to increase the probability of capture, then a similar increase would be expected when the voltage polarity is switched back from negative to positive, when in fact there is instead a suppression.

FIG. 8B is a plot of the fraction of molecules that were recaptured within the 500 ms duration of voltage bias polarity reversal, as a function of the selected time delay between the detection of initiation of forward translocation and the voltage polarity reversal. The dashed line represents the prediction of the drift-diffusion model discussed below. This plotted data indicates that the probability that a molecule was recaptured after a voltage reversal depended on the time between the initial translocation event and the voltage bias reversal. The only molecule having an awareness of this time is the molecule that first translocated the pore in the forward direction and thereby triggered the reversal. Thus, it is proven certain by this data that the recapture experiment did indeed produce two translocations of the same molecule.

The capture-recapture experiment described above was conducted including a time delay period, between detection of initial translocation and voltage polarity reversal, set at 2 ms, 3 ms, 4 ms, 8 ms, 16 ms, and 32 ms. FIGS. 9A-9F are histograms of the probability for a molecule to re-translocate the nanopore for each of these time delays. Each bar in the plots represents the fraction of forward-translocated molecules recaptured in the 1 ms interval centered about the corresponding time. The bold line represents the prediction of the drift-diffusion model discussed below. From the plots, it is shown that for a time delay period less than 4 ms, most molecules arrived at the nanopore and translocated the nanopore in less than 10 ms. It is further shown that both the distribution of recapture times and the overall recapture success rate depend strongly on the duration of the delay period prior to the voltage polarity reversal.

To analyze the results of these molecular capture-recapture experiments further, the dynamics of molecular motion are considered. The drift-diffusion expression for a spherically symmetric distribution of DNA molecules near a nanopore is given as:

$$\frac{\partial c(r, t)}{\partial t} = \frac{1}{r^2}\frac{\partial}{\partial r}r^2\left(\frac{\mp|\mu I|}{2\pi\sigma r^2}c(r, t) + D\frac{\partial c(r, t)}{\partial r}\right) \quad (1)$$

where − implies motion away from the pore and + motion towards it.

With dimensionless units of length, $x=r/L$ and time, $s=t/\tau$, with $$L = \frac{\mu I}{2\pi\sigma D}$$

and $\tau=L^2/D$, the expression becomes:

$$\frac{\partial c(x, s)}{\partial s} = \frac{1}{x^2}\frac{\partial}{\partial x}\left(\mp c(x, s) + x^2\frac{\partial c(x, s)}{\partial x}\right). \quad (2)$$

The molecular capture-recapture experiments described above were modeled by solving numerically this drift-diffusion expression for these initial and boundary conditions:

$$c(r, 0) = \frac{\delta(r - r_0)}{2\pi r_0^2} \quad (3)$$

$$c(r_c, t) = 0$$

$$\frac{\partial c}{\partial r}(\infty, t) = 0$$

where $r_0$ is the initial distance of a molecular from the nanopore, and was taken to be the average distance from a wall for a Gaussian chain with one end tethered at the wall, 30 nm for the 4 kbp DNA and 37 nm for the 6 kbp DNA employed in the experiments. The capture radius, $r_c$, at which the molecule was assumed to translocate through the pore with unit efficiency, was chosen to be 5 nm less than $r_0$. It was found that the results had little dependence on the values chosen for these radii, as long as they were much less than the outer recapture distance, L. A reflecting boundary condition at infinity was chosen to simplify computation.

Figure 10B:
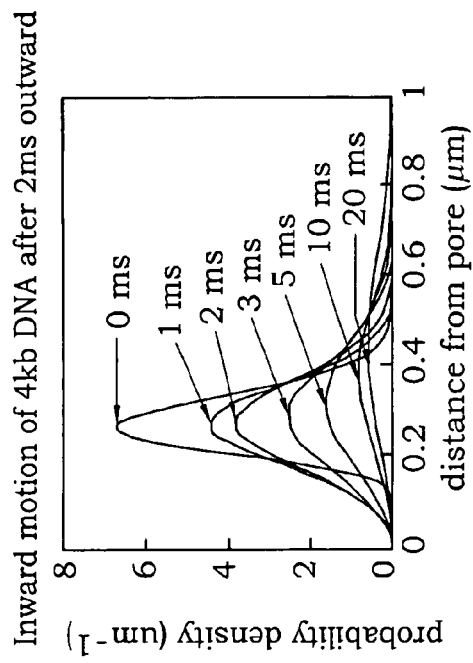
FIGS. 10A-10D are plots of calculated probability density and molecular recapture, respectively, in an experimental molecular capture and recapture system in accordance with the invention.
Figure 10D:
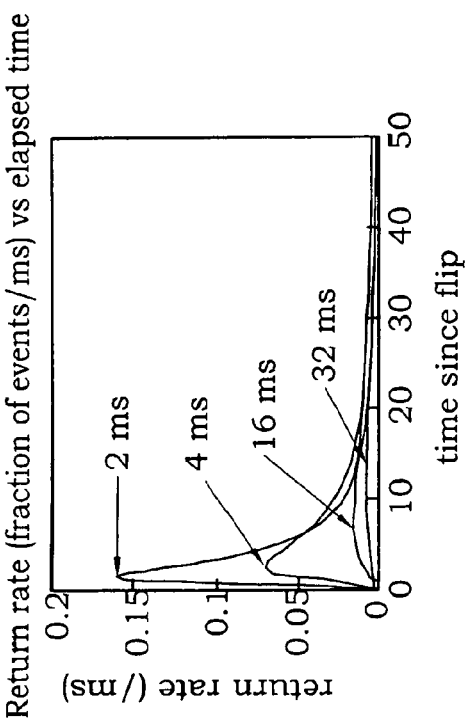
Figure 10A:
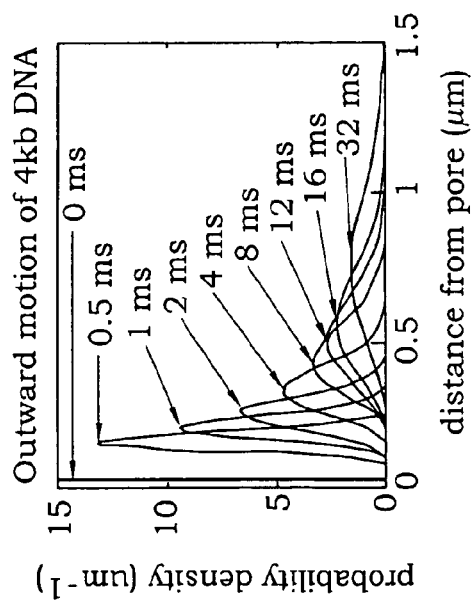
Figure 10C:
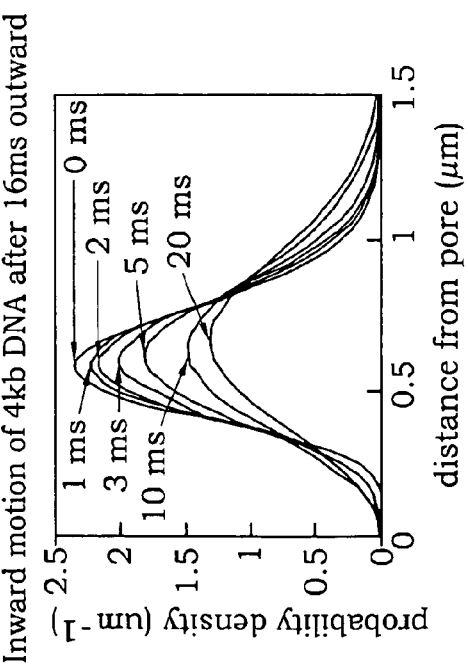

FIGS. 10A-10D plot the results of these calculations for 4 kb dsDNA at 3.5 nA in 1 M KCl. FIGS. 10A-10D plot the linear probability density $p(r)=2\pi r^2 c(r)$, where $c(r)$ is the volume density, and $p(r)dr$ represents the probability a molecule is found between r and r+dr. FIG. 10A shows the evolution of the probability density with time as the current is directed away from the nanopore. The initial probability density is a delta function at 30 nm. The peak probability moves away from the nanopore with time, but due to diffusion, there is still a significant chance the molecule remains within 500 nm of the nanopore, even after 30 ms. FIGS. 10B-10C show the evolution of the probability densities plotted in FIG. 10A after the voltage is reversed and the molecule is directed towards the nanopore. FIG. 10B provides the results of the simulation of an experiment in which the voltage was reversed after 2 ms, while FIG. 10C simulates one in which the voltage was reversed after 16 ms of outbound travel. Note that although the net flux of molecules is inward, the probability distribution eventually skews away from the nanopore. This is because molecules close to the nanopore translocate and are removed from the distribution.

FIG. 10B is a plot of the probability that a molecule would translocate the nanopore within the dimensionless time $t/\tau$ for various dimensionless starting radii, $x_0=r_0/L$. Most translocations were found to occur within $\frac{1}{2}\tau$ for starting distances less than the outer recapture distance, L. FIG. 10B is a plot of the probability that a molecule would return to the nanopore within $\frac{1}{2}\tau$ versus the starting distance. A molecule that starts at $x_0=0.4$ is found to reach the nanopore within $\frac{1}{2}\tau$ 85% of the time. For these simulations, the dimensionless capture radius, at which instantaneous translocation was assumed, was 0.01.

With the voltage polarity of the molecular driving force set such that the electric force is directed away from the nanopore, the steady state concentration of DNA in the cis reservoir is expressed as:

$$c(r) = c_\infty \exp\left(-\frac{L}{r}\right), \quad (4)$$

where $c_\infty$ is the concentration of DNA far from the nanopore. It is unclear a priori how closely the concentration approaches this equilibrium value in the 500 ms voltage reversal window, so the expression is solved for the initial and boundary conditions given as:

$$c(r,0)=c_\infty$$

$$c(r_c,t)=0$$

$$c(\infty,t)=c_\infty \quad (5)$$

for 500 ms with the drift directed outward. This solution was employed as the initial condition when solving for inward directed drift to produce the predicted forward molecular translocation rates shown in the plot of FIG. 8A.

EXAMPLE II

The molecular capture-recapture system of Example I was modified to operate as a single-molecule spatial trap. A dilute concentration, 12 ng/μL, of a mixture of 5.4 kbp and 10 kbp DNA molecules was employed in the solution. This mixture of differing molecules was employed to enable the detection of a substitution of one molecule for another in the trap; if a second molecule were to displace the trapped molecule, there is a 50% chance that the detected molecular length would change, given the solution mixture. The relatively low concentration of molecules was employed here to decrease the probability that a second molecule from the cis reservoir would be close enough to be captured and replace an initially-trapped molecule. Also, at this concentration, under forward-translocation voltage bias polarity, new molecules arrived at the nanopore at a rate of under 0.4 Hz. Under reverse-translocation voltage bias polarity, the background arrival rate was an order of magnitude less. It was possible to detect, by measuring the event charge deficit, as defined above, substitutions of 5.4 kbp molecules for 10 kbp molecules and vice versa in the trap.

In this single-molecule trapping experiment, the feedback control was modified to trigger a reversal in voltage polarity 2 ms after a detection of molecular translocation of the nanopore in either direction. A molecular driving force voltage bias magnitude of 150 mV was employed, and the excess electrical current due to membrane charging was partially compensated for by pipette capacitance compensation on the Axopatch 200B.

Figure 12B:
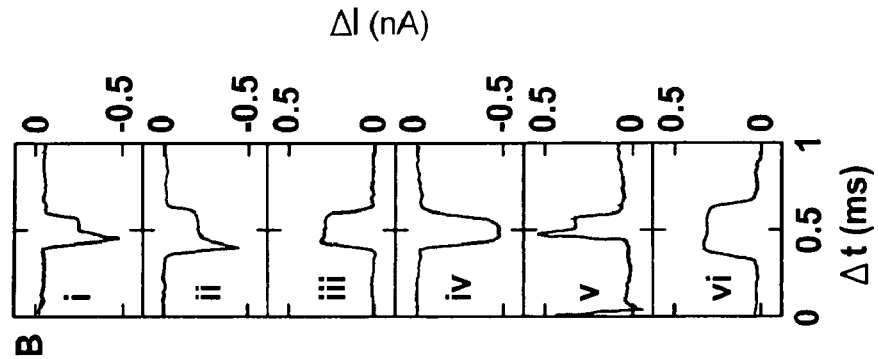
FIGS. 12A-12B are plots of current blockage and applied voltage, and an enlarged current blockage view, respectively, for an experimental spatial trap in accordance with the invention.
Figure 12A:
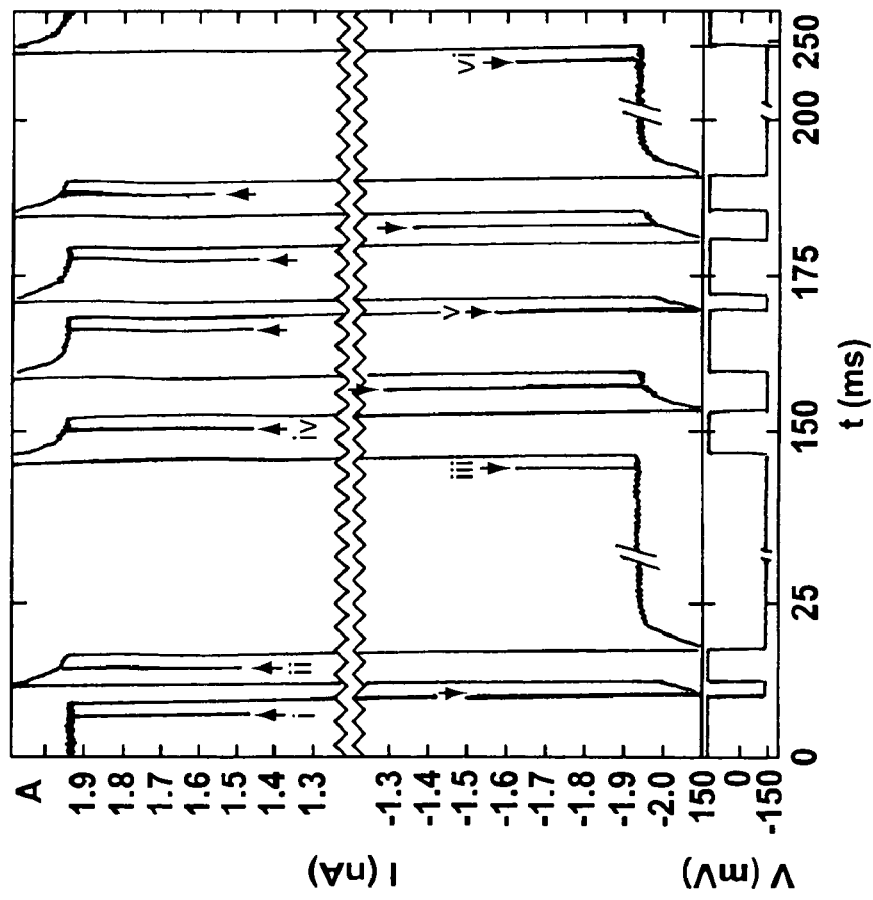

FIG. 12A is a plot of the measured voltage and current traces for the single-molecule trap, here monitored for a 10 kbp dsDNA molecule translocated through the nanopore twelve times over 250 ms. The current trace represents the ionic current through the nanopore as a function of time. For clarity in the plot, 2.4 nA are excised from the center of the current axis, and the time axis has also been compressed. The short pulses, marked with arrows, show ionic current being blocked as the molecule translocates the nanopore. 2 ms after each detected passage, the voltage bias was reversed. The molecule was initially captured at positive voltage bias. The exponential settling at the beginning of each transition results from charging of the membrane capacitance. FIG. 12B is a plot of expanded ionic current traces resulting from separate passages of the 10 kbp molecule through the nanopore. Each is labeled with a roman numeral that identifies the portion of the current trace in FIG. 12A from which it was taken. This experiment provides convincing proof of principal that the voltage-biased solid state nanopore capture-recapture system of the invention with active feedback can spatially trap a single molecule in the vicinity of the nanopore for repeated examination of the molecule.

With these examples and the description above, it is demonstrated that the invention provides a nanopore-based system for carrying out molecular capture and recapture cycles, for determining characteristics of molecules, especially polymeric molecules such as nucleic acids and proteins. By recapturing a molecule after the molecule translocates a nanopore, that molecule can be re-examined many times, e.g., to reduce uncertainties or eliminate ambiguities in data that may be perceived during or after a first capture and translocation of the nanopore. In-depth characterization of single molecules, for example, for determining the sequence of a DNA molecule with the nanopore system of the invention, either alone or as part of a more complicated system, is enabled by the molecular capture and recapture cycles of the invention. The invention further enables techniques for probing and controlling the dynamics of molecules in free solution on sub-millisecond time scales and sub-micron length scales for, e.g., characterizing the effects of species in the solution on characteristics of the molecules. Repeated translocation of the nanopore by the same molecule enables the ability to spatially trap, characterize, and manipulate the molecule in solution for extended times, in analogy to methods in atomic physics to localize and manipulate elementary forms of matter.

It is recognized, of course, that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A molecular analysis system comprising:
a structure including a nanopore;
first and second fluidic reservoirs, the two reservoirs being fluidically connected via the nanopore, each reservoir containing an ionic solution characterized by an ionic conductivity, σ, and one of the reservoirs including a molecule, under analysis, that is characterized by a mobility, μ, and a diffusion constant, D, in the ionic solution;
a detector connected to detect ionic current flow, I, through the nanopore, as an indicator of molecular species translocation through the nanopore, from one of the two fluidic reservoirs to the other of the two fluidic reservoirs; and
a controller and control circuit that apply a changing voltage bias between the first and second reservoirs causing a plurality of nanopore translocations by the molecule under analysis, each voltage bias change occurring at a time, after detection of a molecular nanopore translocation, that is no greater than about a time, t(L), where:

$$t(L) = \frac{|\mu I|^2}{12\pi^2 \sigma^2 D^3},$$

to maintain the molecule under analysis within a hemispherical recapture field distance, L, measured from the nanopore in each reservoir after each nanopore translocation, so that the molecule under analysis is caused to repeatedly translocate the nanopore, where:

$$L = \frac{|\mu I|}{2\pi \sigma D}.$$

2. The system of claim 1 wherein the structure including the nanopore is characterized by an electrical capacitance, and wherein the controller generates a voltage bias change, in response to detection of a molecular nanopore translocation, after a time delay during which the nanopore structure is capacitively charged up.

3. The system of claim 1 wherein the controller is configured to generate a sequence of control signals that produce time-dependent changing voltage bias conditions between the two reservoirs at the nanopore to induce the molecular species under analysis to re-translocate the nanopore a selected number of times.

4. The system of claim 1 wherein the controller is configured to generate a control signal that produces the changing voltage bias in response to detection of molecular species translocation of the nanopore from the first fluidic reservoir to the second fluidic reservoir and to generate the control signal after a prespecified translocation duration corresponding to molecular species re-translocation of the nanopore from the second fluidic reservoir to the first fluidic reservoir.

5. The system of claim 1 wherein the detector is configured to detect a translocation duration during molecular species translocation of the nanopore and to detect a re-translocation duration during molecular species re-translocation of the nanopore.

6. The system of claim 1 wherein the changing voltage bias between the first and second reservoirs is of a reversible polarity selected by the controller to induce molecular species translocation and re-translocation in selected directions through the nanopore.

7. The system of claim 1 wherein the detector comprises an amplifier connected to measure ionic current flow through the nanopore as an indicator of molecular species translocation of the nanopore.

8. The system of claim 7 wherein the controller comprises a high pass filter to filter measured current flow.

9. The system of claim 1 wherein the controller includes a comparator with a prespecified threshold to determine if a signal from the detector is indicative of molecular species translocation of the nanopore.

10. The system of claim 1 wherein the structure comprises a membrane.

11. The system of claim 1 wherein the nanopore has a diameter no greater than about 1 micron.

12. The system of claim 1 wherein the nanopore has a diameter no greater than about 100 nm.

13. The system of claim 1 wherein the nanopore has a diameter no greater than about 10 nm.

14. The system of claim 1 wherein the nanopore has a diameter no greater than about 5 nm.

15. The system of claim 1 wherein the molecule under analysis included in one of the fluidic reservoirs comprises macromolecules.

16. The system of claim 1 wherein the molecule under analysis included in one of the fluidic reservoirs comprises molecular components.

17. The system of claim 1 wherein the molecule under analysis included in one of the fluidic reservoirs comprises polymer molecules.

18. The system of claim 1 wherein the molecule under analysis included in one of the fluidic reservoirs comprises biomolecules.

19. The system of claim 1 wherein the molecule under analysis included in one of the fluidic reservoirs comprises components of biomolecules.

20. The system of claim 1 wherein the molecule under analysis included in one of the fluidic reservoirs comprises DNA molecules.

21. The system of claim 20 wherein the controller and control circuit generate each voltage bias change at a time that is between about 0.5 ms and about 1 ms after detection of a molecular nanopore translocation.

22. The system of claim 1 wherein the molecule under analysis included in one of the fluidic reservoirs comprises oligonucleotides.

23. The system of claim 1 wherein the molecule under analysis included in one of the fluidic reservoirs comprises nucleotides.

24. The system of claim 1 wherein the molecule under analysis included in one of the fluidic reservoirs comprises at least one molecule including at least one attached species differing from the molecule in electronic charge.

25. The system of claim 1 wherein the molecule under analysis included in one of the fluidic reservoirs comprises at least one molecule including at least one attached species differing from the molecule in diameter.

26. The system of claim 1 wherein one of the fluidic reservoirs includes in solution a species that is reactive with the molecular species under analysis.

27. The system of claim 26 wherein the reactive species comprises a protein.

28. The system of claim 26 wherein the reactive species comprises a complementary nucleic acid.

29. The system of claim 26 wherein the reactive species comprises an ionic species.

30. The system of claim 1 wherein one of the fluidic reservoirs includes a solution that is characterized by condition that is reactive with the molecular species under analysis.

31. The system of claim 1 wherein the two fluidic reservoirs are configured with differing fluids.

32. The system of claim 31 wherein the two fluidic reservoirs are configured with fluids of differing pH.

33. The system of claim 31 wherein the two fluidic reservoirs are configured with fluids of differing concentrations of a solvent.

34. The system of claim 31 wherein the two fluidic reservoirs are configured with fluids of differing concentrations of a solute.

35. The system of claim 31 wherein the two fluidic reservoirs are configured with fluids of differing temperature.

36. A method for molecular analysis comprising:
translocating a molecular species under analysis a plurality of times through a nanopore in a structure between two fluidic reservoirs separated by the structure, each reservoir containing an ionic solution characterized by an ionic conductivity, $\sigma$, and one of the reservoirs including the molecule under analysis, the molecule being characterized by a mobility, $\mu$, and a diffusion constant, $D$, in the ionic solution;
detecting ionic current flow, $I$, through the nanopore, as an indicator of molecular species translocation through the nanopore, from one of the two fluidic reservoirs to the other of the two fluidic reservoirs; and
applying a changing voltage bias between the first and second reservoirs causing the plurality of nanopore translocations by the molecule under analysis, each voltage bias change occurring at a time, after detection of a molecular nanopore translocation, that is no greater than about a time, $t(L)$, where:

$$t(L) = \frac{|\mu I|^2}{12\pi^2 \sigma^2 D^3},$$

to maintain the molecule under analysis within a hemispherical recapture field distance, $L$, measured from the nanopore in each reservoir after each nanopore translocation, so that the molecule under analysis is caused to repeatedly translocate the nanopore, where:

$$L = \frac{|\mu I|}{2\pi\sigma D}$$

37. The method of claim 36 wherein repeated translocation of the nanopore by the molecular species comprises 2 translocations of the nanopore.

38. The method of claim 36 wherein repeated translocation of the nanopore by the molecular species comprises more than 2 translocations of the nanopore.

39. The method of claim 36 wherein repeated translocation of the nanopore by the molecular species comprises more than 10 translocations of the nanopore.

40. The method of claim 36 wherein repeated translocation of the nanopore by the molecular species comprises more than 50 translocations of the nanopore.

41. The method of claim 36 wherein a voltage bias change to induce the molecular species to repeatedly translocate the nanopore is produced in response to detection of a molecular nanopore translocation after a prespecified delay period during which the nanopore structure is capacitvely charged up.

42. The method of claim 36 wherein detecting molecular species translocation of the nanopore comprises determining translocation duration.

43. The method of claim 36 wherein applying a changing voltage bias between the first and second reservoirs comprises applying a sequence of voltage polarity reversals to induce repeated molecular species translocation through the nanopore between the fluidic reservoirs.

44. The method of claim 36 wherein the two fluidic reservoirs between which the molecular species is translocated comprise differing fluids.

45. The method of claim 36 wherein the molecular species comprises a macromolecule.

46. The method of claim 36 wherein the molecular species comprises a molecular component.

47. The method of claim 46 wherein the molecular component comprises a biomolecule component.

48. The method of claim 47 wherein the biomolecule component comprises a nucleotide fragment.

49. The method of claim 47 wherein the biomolecule component comprises an oligonucleotide.

50. The method of claim 47 wherein molecular species comprises a biomolecule.

51. The method of claim 36 wherein the molecular species comprises a polymer molecule.

52. The method of claim 36 wherein the molecular species comprises DNA.

53. The method of claim 52 wherein each voltage bias change occurs at a time that is between about 0.5 ms and about 1 ms after detection of a molecular translocation through the nanopore.

54. The method of claim 36 wherein the molecular species includes at least one molecule including at least one attached species differing from the molecule in electronic charge.

55. The method of claim 36 wherein the molecular species includes at least one molecule including at least one attached species differing from the molecule in diameter.

56. The method of claim 36 further comprising changing a characteristic of at least one of the fluidic reservoirs over time during the repeated molecular species translocation through the nanopore.

57. The method of claim 56 wherein changing a characteristic of at least one of the fluidic reservoirs comprises changing a reservoir temperature.

58. The method of claim 56 wherein changing a characteristic of at least one of the fluidic reservoirs comprises changing a reservoir pH.

59. The method of claim 56 wherein changing a characteristic of at least one of the fluidic reservoirs comprises changing a reservoir ionic concentration.

60. The method of claim 56 wherein changing a characteristic of at least one of the fluidic reservoirs comprises providing a reactive species in one of the reservoirs.

61. A method for exposing a molecular species to a reactive environment comprising:
translocating a molecular species through a nanopore from a first fluidic reservoir to a second fluidic reservoir, each reservoir containing an ionic solution characterized by an ionic conductivity, $\sigma$, and one of the reservoirs including a molecule, under analysis, that is characterized by a mobility, $\mu$, and a diffusion constant, D, in the ionic solution, and one of the reservoirs-containing an environment that is reactive with the molecular species;
detecting ionic current flow, I, through the nanopore, as an indicator of molecular species translocation through the nanopore, from one of the two fluidic reservoirs to the other of the two fluidic reservoirs; and
applying a changing voltage bias between the first and second reservoirs causing the plurality of nanopore translocations by the molecule under analysis, each voltage bias change occurring at a time, after detection of a molecular nanopore translocation, that is no greater than about a time, t(L), where:

$$t(L) = \frac{|\mu I|^2}{12\pi^2 \sigma^2 D^3},$$

to maintain the molecule under analysis within a hemispherical recapture field distance, L, measured from the nanopore in each reservoir after each nanopore translocation, so that the molecule under analysis is caused to repeatedly translocate the nanopore, where:

$$L = \frac{|\mu I|}{2\pi\sigma D}$$

62. The method of claim 61 wherein the environment that is reactive with the molecular species comprises a reactive species in fluid.

63. The method of claim 61 wherein the environment that is reactive with the molecular species comprises a protein.

64. The method of claim 61 wherein the environment that is reactive with the molecular species comprises a biomolecule.

65. A method for sequencing a genome comprising:
providing a plurality of nucleotide fragments from a genome in a first fluidic reservoir;
translocating each nucleotide fragment a selected number of times through a nanopore in a structure between the first fluidic reservoir and a second fluidic reservoir separated from the first reservoir by the structure, each reservoir containing an ionic solution characterized by an ionic conductivity, $\sigma$, with the nucleotide fragments characterized by a mobility, $\mu$, and a diffusion constant, D, in the ionic solution;
detecting each nucleotide fragment as that nucleotide fragment translocates the nanopore by detecting ionic current flow, I, through the nanopore, as an indicator of nucleotide fragment translocation through the nanopore, from one of the two fluidic reservoirs to the other of the two fluidic reservoirs; and applying a changing voltage bias between the first and second reservoirs causing the plurality of nanopore translocations by the nucleotide fragments, each voltage bias change occurring at a time, after detection of a nucleotide fragment translocation through the nanopore, that is no greater than about a time, t(L), where:

$$t(L) = \frac{|\mu I|^2}{12\pi^2 \sigma^2 D^3},$$

to maintain the nucleotide fragments within a hemispherical recapture field distance, L, measured from the nanopore in each reservoir after each nanopore translocation, so that the nucleotide fragments are caused to repeatedly translocate the nanopore, where:

$$L = \frac{|\mu I|}{2\pi \sigma D}$$

66. The method of claim 65 wherein each nucleotide fragment is translocated through the nanopore at least 5 times.

67. The method of claim 65 wherein each nucleotide fragment is translocated through the nanopore at least 10 times.

68. The method of claim 65 wherein each nucleotide fragment is translocated through the nanopore at least 20 times.

69. The method of claim 65 wherein detecting each nucleotide fragment comprises determining if a nucleotide fragment has previously been detected and translocated the selected number of times, and if so, discarding that nucleotide fragment into the second reservoir by discontinuing further translocations of that nucleotide fragment back to the first reservoir.

70. Method of claim 65 wherein detecting each nucleotide fragment comprises determining if a nucleotide fragment has previously been detected and translocated the selected number of times, and if not, translocating the nucleotide fragment through the nanopore at least one additional time.

71. The method of claim 65 wherein each voltage bias change occurs at a time that is between about 0.5 ms and about 1 ms after detection of a nucleotide fragment translocation through the nanopore.

* * * * *

UNITED STATES PATENT AND TRADEMARK OFFICE
CERTIFICATE OF CORRECTION

PATENT NO. : 8,273,532 B2
APPLICATION NO. : 12/286787
DATED : September 25, 2012
INVENTOR(S) : Marc H. Gershow, Jene A. Golovchenko and Daniel Branton It is certified that error appears in the above-identified patent and that said Letters Patent is hereby corrected as shown below:

In the Specification

Column 1, Line 14, delete "Contract No."; Line 14, "5RO0HG003703" should be changed to --HG003703--; and Line 14, "NIH" should be changed to --the National Institutes of Health--.

Signed and Sealed this
Fourteenth Day of May, 2024

Katherine Kelly Vidal
*Director of the United States Patent and Trademark Office*